United States Patent
Tabata et al.

(10) Patent No.: US 10,801,007 B2
(45) Date of Patent: Oct. 13, 2020

(54) CELL DETECTION DEVICE AND CELL DETECTION METHOD

(71) Applicant: SYSMEX CORPORATION, Kobe-shi, Hyogo (JP)

(72) Inventors: Seiichiro Tabata, Kobe (JP); Masatoshi Yanagida, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 16/591,670

(22) Filed: Oct. 3, 2019

(65) Prior Publication Data

US 2020/0032196 A1    Jan. 30, 2020

Related U.S. Application Data

(63) Continuation of application No. 15/159,089, filed on May 19, 2016, now Pat. No. 10,513,679.

(30) Foreign Application Priority Data

May 20, 2015 (JP) ................................. 2015-103254

(51) Int. Cl.
*C12M 1/34* (2006.01)
*G01N 15/14* (2006.01)
(Continued)

(52) U.S. Cl.
CPC ............ *C12M 41/46* (2013.01); *C12M 31/10* (2013.01); *C12M 47/04* (2013.01); *G01N 1/40* (2013.01);
(Continued)

(58) Field of Classification Search
None
See application file for complete search history.

(56) References Cited

U.S. PATENT DOCUMENTS

| 5,853,994 A * | 12/1998 | Gopinathan | ......... G01N 29/032 435/6.11 |
| 2006/0177348 A1 * | 8/2006 | Yasuda | ............. B01L 3/502715 422/73 |

(Continued)

FOREIGN PATENT DOCUMENTS

| EP | 2022843 A1 * | 2/2009 | ........... G01N 33/491 |
| JP | 2005-524831 A | 8/2005 | |

(Continued)

OTHER PUBLICATIONS

Office action dated Oct. 8, 2019 in a counterpart of Japanese patent application.

(Continued)

*Primary Examiner* — Jill A Warden
*Assistant Examiner* — Brittany I Fisher
(74) *Attorney, Agent, or Firm* — Metrolex IP Law Group, PLLC

(57) ABSTRACT

A cell detection device and a cell detection method is provided with which it is possible to efficiently acquire images of cells to be measured. Cell detection device comprises flow cell through which a measurement specimen that contains particles is caused to flow, particle detector for detecting the particles in the measurement specimen supplied to flow cell, particle sorter for sorting particles that satisfy a detection condition and other particles on the basis of the result of detection performed by particle detector, specimen supply part for supplying, to flow cell, an image-capture specimen that includes detection-condition-satisfying particles that have been sorted by particle sorter, and particle-image-capture part for capturing images of the particles in the sorted image-capture specimen supplied to flow cell.

20 Claims, 22 Drawing Sheets

(51) Int. Cl.
*G01N 15/10* (2006.01)
*G01N 1/40* (2006.01)
*C12M 1/00* (2006.01)

(52) U.S. Cl.
CPC ....... *G01N 15/147* (2013.01); *G01N 15/1459* (2013.01); *G01N 2015/1006* (2013.01); *G01N 2015/144* (2013.01)

(56) References Cited

U.S. PATENT DOCUMENTS

| | | | |
|---|---|---|---|
| 2009/0198168 A1* | 8/2009 | Hiruma | A61M 1/36 604/6.08 |
| 2012/0091059 A1* | 4/2012 | Beer | B01L 3/502761 210/634 |
| 2012/0160746 A1* | 6/2012 | Thorslund | B01L 3/502761 209/552 |
| 2014/0008307 A1* | 1/2014 | Guldiken | B01L 3/502761 210/748.05 |

FOREIGN PATENT DOCUMENTS

| | | | | |
|---|---|---|---|---|
| WO | WO-03089158 A1 * | 10/2003 | | B07C 5/34 |
| WO | 2014/146030 A1 | 9/2014 | | |

OTHER PUBLICATIONS

Office action dated Jul. 21, 2020 in a counterpart European patent application.

* cited by examiner

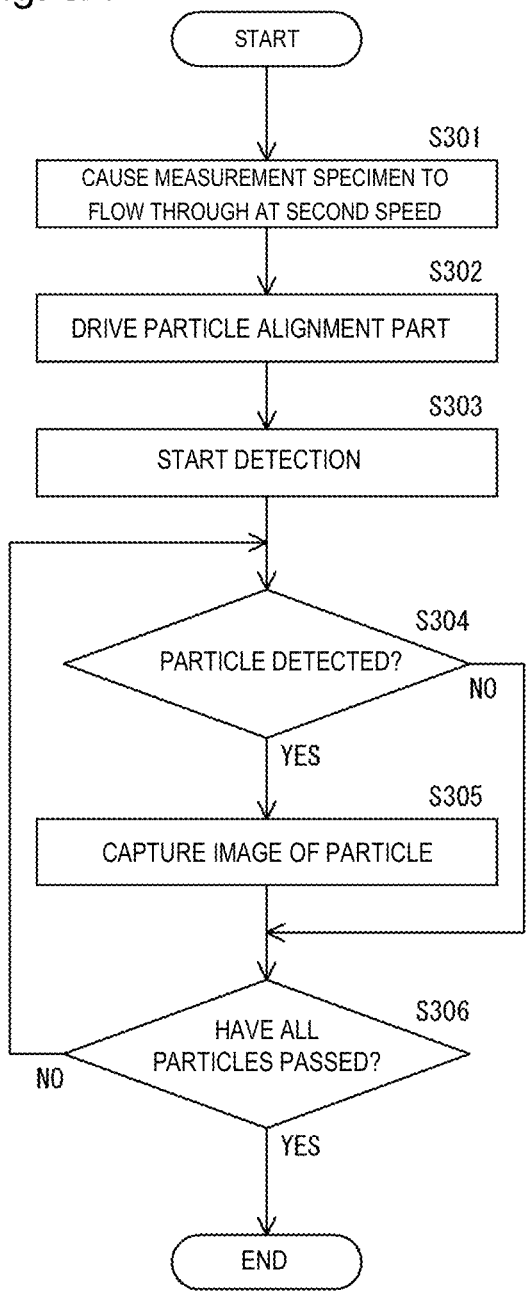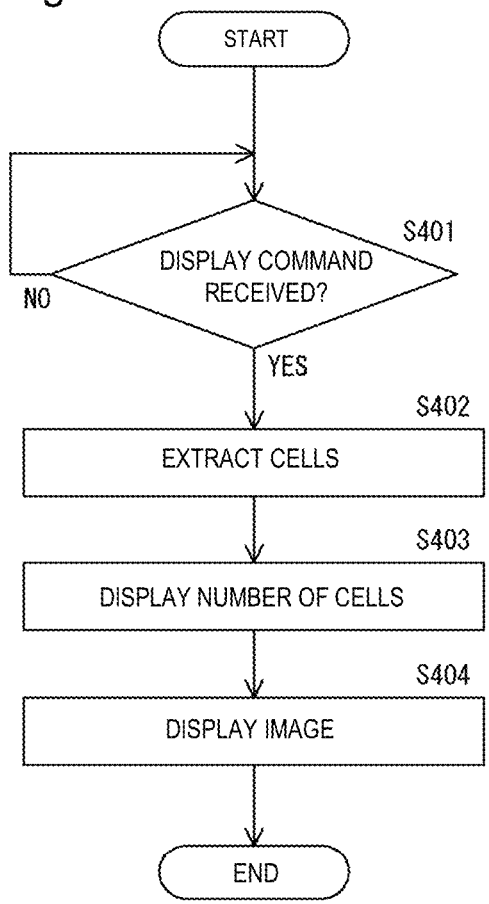
Fig. 6A
Fig. 6B

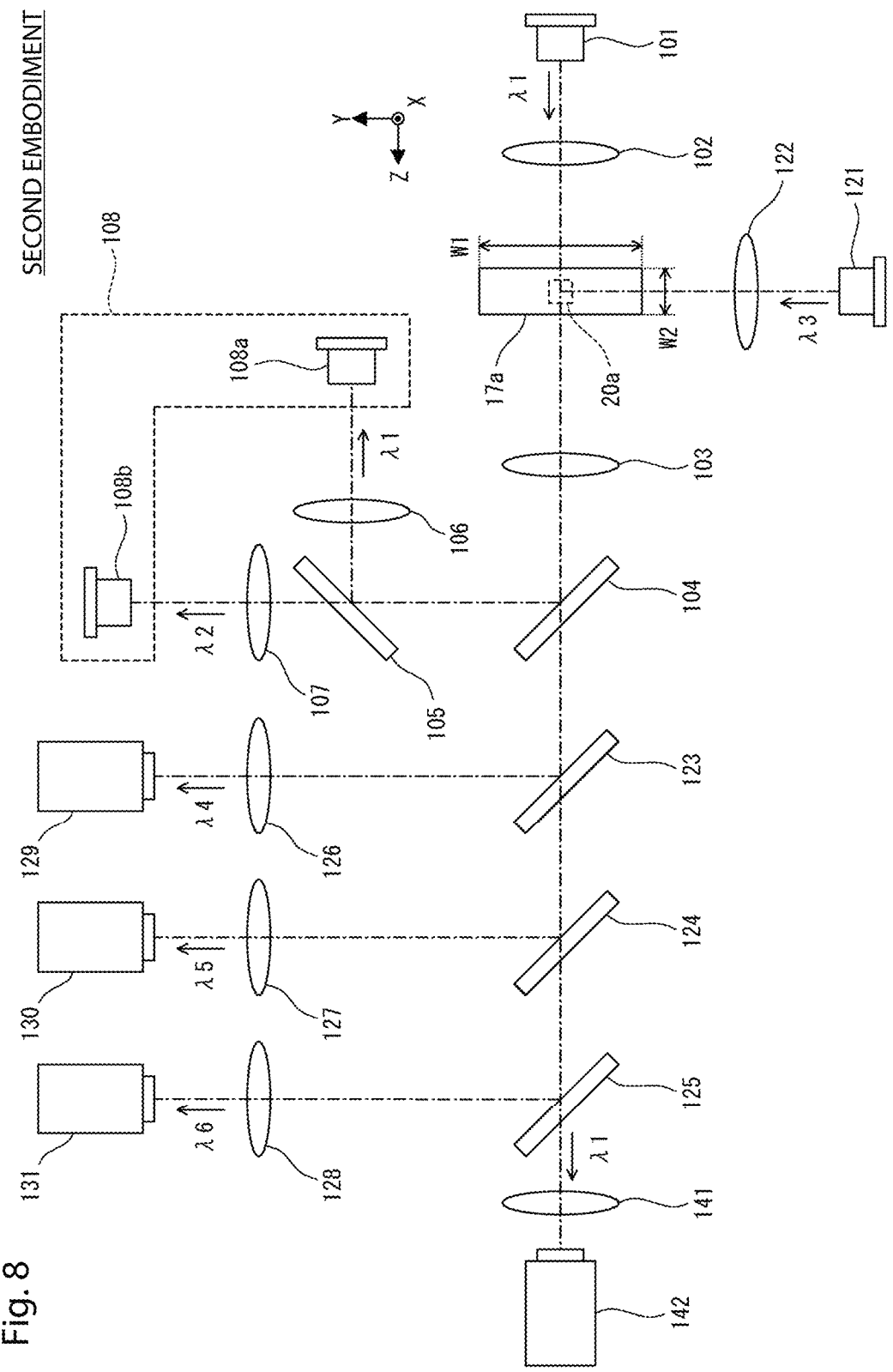

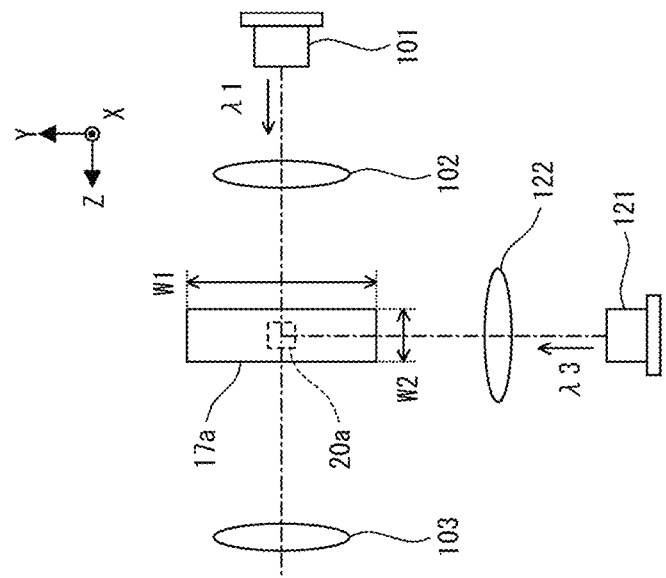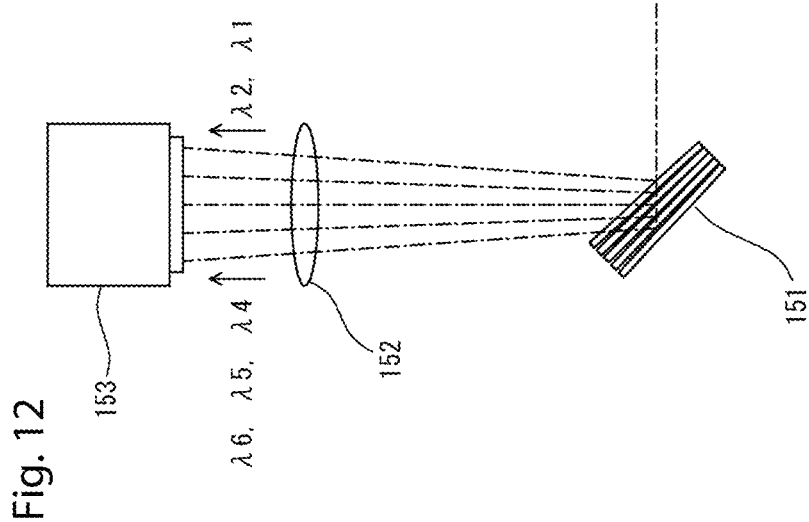
Fig. 12

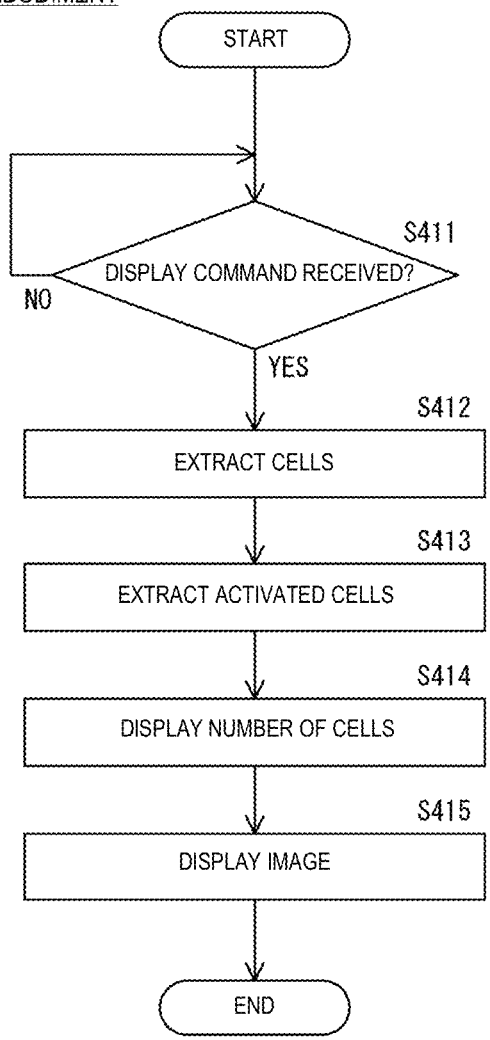

ACTIVATED

NOT ACTIVATED

CELL DETECTION DEVICE AND CELL DETECTION METHOD

CROSS REFERENCE TO RELATED APPLICATION

This application is a continuation of application Ser. No. 15/159,089, filed on May 19, 2016, which is based upon and claims the benefit of priority from the prior Japanese Patent Application No. 2015-103254, filed on May 20, 2015, the entire contents of all of which are incorporated herein by reference.

BACKGROUND

The disclosure relates to a cell detection device and a cell detection method.

Devices comprising a particle detector that detects particles in a measurement specimen flowing through a flow cell, and an image-capture part that captures images of the particles in the measurement specimen flowing through the flow cell are known as detection/measurement devices in which a flow cytometer is used. For example, in the detection/measurement device described in Japanese Laid-open Patent Publication No. 63-94156 (Patent Document 1), a configuration for capturing images of cells is arranged downstream of a cell detection part. In the detection/measurement device, cells in a measurement specimen flowing through a flow cell are irradiated with laser light, and images of the cells in the measurement specimen are captured using a CCD camera, a signal generated by the cells being used as a trigger.

SUMMARY

A cell detection device according to a first aspect of embodiment comprises: a flow cell through which a measurement specimen that contains particles is caused to flow; a particle detector for detecting the particles in the measurement specimen supplied to the flow cell; a particle sorter for sorting particles that satisfy a detection condition and other particles on the basis of the result of detection performed by the particle detector; a specimen supply part for supplying, to the flow cell, an image-capture specimen that includes detection-condition-satisfying particles that have been sorted by the particle sorter; and a particle-image-capture part for capturing images of the particles in the sorted image-capture specimen supplied to the flow cell.

A cell detection method according to a second aspect of embodiment comprises: causing a measurement specimen that contains particles to flow through a flow cell; detecting the particles in the measurement specimen supplied to the flow cell; sorting particles that satisfy a detection condition and other particles on the basis of the result of the particle detection; supplying, to the flow cell, an image-capture specimen that includes sorted particles that satisfy the detection condition; and capturing images of the particles in the sorted image-capture specimen supplied to the flow cell.

BRIEF DESCRIPTION OF THE DRAWINGS

FIG. 6A is a flowchart illustrating the processes initiated by an image-capture process according to the first embodiment, and FIG. 6B is a flowchart illustrating a display process performed by the cell detection device according to the first embodiment;

FIG. 8 is a schematic diagram illustrating the configuration of a particle detector and a particle-image-capture part according to a second embodiment;

FIG. 12 is a schematic diagram illustrating the configuration of a particle detector and a particle-image-capture part according to a fourth embodiment;

FIG. 18 is a flowchart illustrating the processes performed by a cell detection device according to a seventh embodiment;

DETAILED DESCRIPTION

First Embodiment

A first embodiment is described applying to a device for capturing images of circulating tumor cells contained in a blood sample as test cells. The term "circulating tumor cell" is referred to below as "CTC." CTCs derived from advanced-cancer cells circulate along with the flow of blood or lymph and spreads to distant organs. It has been found that CTCs in the blood are useful as a prognostic factor, as well as in assessing therapeutic effect, in patients suffering from breast cancer, prostate cancer, colorectal cancer, or another metastatic cancer. Measuring CTCs is effective when a prognosis is to be predicted with respect to progression-free survival rate, overall survival rate, and the like, or where the therapeutic effect is to be assessed. There is a trace amount of CTCs circulating in the blood; i.e., approximately several CTCs to several tens of CTCs in 10 mL of blood.

Figure 1:
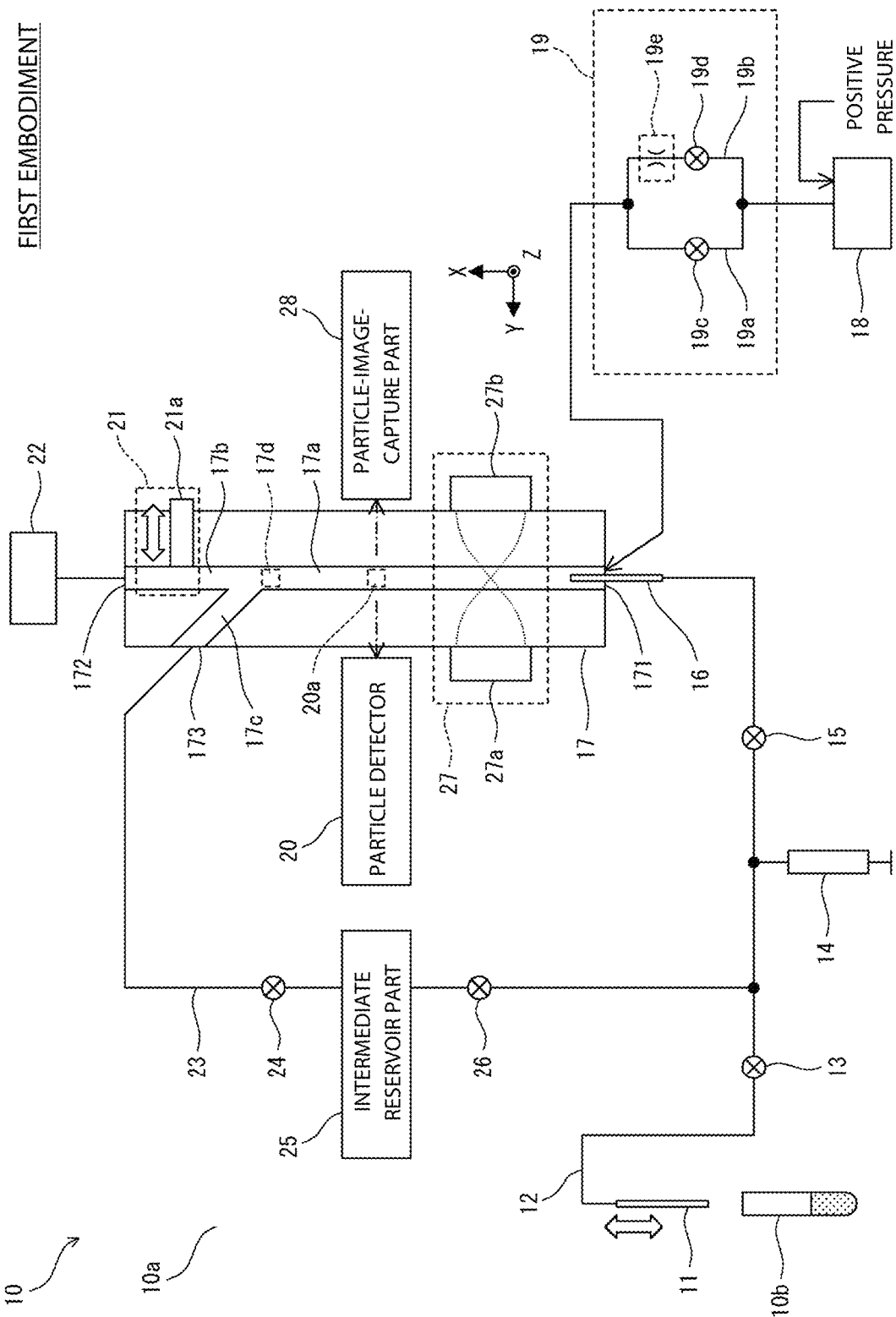
FIG. 1 is a schematic diagram illustrating the configuration of a cell detection device according to a first embodiment.

As illustrated in FIG. 1, cell detection device 10 comprises specimen supply part 10a, flow cell 17, sheath liquid supply part 18, speed-change part 19, particle detector 20, particle sorter 21, waste fluid reservoir part 22, particle alignment part 27, and particle-image-capture part 28. Specimen supply part 10a comprises nozzle 11, supply flow path 12, valve 13, syringe 14, valve 15, jet nozzle 16, recirculation flow path 23, valve 24, intermediate reservoir part 25, and valve 26. The valves provided to cell detection device 10 are electromagnetically openable/closable.

Specimen supply part 10a supplies a measurement specimen accommodated in specimen container 10b to flow cell 17, and after the sorting of particles by particle sorter 21 is complete, supplies a measurement specimen that includes detection-condition-satisfying particles that have been sorted by particle sorter 21 to flow cell 17. The measurement specimen that includes detection-condition-satisfying particles that have been sorted by particle sorter 21 is referred to below as an "image-capture specimen."

Specimen container 10b accommodates a particle-containing measurement specimen. Measurement specimens are prepared in advance by admixing the following reagents into perinatal samples collected from humans: hemolytic agents that cause hemolysis of red blood cells; reagents containing CD45 labeled antibodies for detecting white blood cells; reagents containing a Ch17 probe that bonds to chromosome 17; reagents containing a Her2 probe that bonds to the Her2 gene; reagents containing antibodies that bond to a Ch17 probe labeled using Alexa 488 dye; reagents containing antibodies that bond to a Her2 probe labeled using PE dye; and reagents containing 7AAD dye that stain nuclei.

When these reagents are admixed into the sample, the red blood cells are hemolyzed by the action of the hemolytic agent. CD45 antigens expressed on the surface of the white blood cells are labeled by the CD45 labeled antibodies. Chromosome 17 is labeled by the Alexa 488 dye. The Her2 gene is labeled by the PE dye. The nuclei are stained by the 7AAD dye. When the Alexa 488, PE, and 7AAD dyes are irradiated with 488-nm-wavelength light emitted from light source 121 (described later), fluorescence of different wavelengths is excited. FITC dye may be used instead of Alexa 488 dye, and PE-Cy7 dye may be used instead of PE dye.

When the excitation wavelengths of the dye that labels the antibodies bonded to the Ch17 probe, the dye that labels the antibodies boned to the Her2 probe, and the dye that stains the nuclei are different, light source 121 (described later) is changed to a light source that emits light of different spectra that correspond to the excitation wavelengths of the dyes. A stroboscopic laser in which light-emission elements are mounted on a substrate can be used as such a light source. Alternatively, light source 121 may be configured such that laser beams emitted from semiconductor lasers are combined by a dichroic mirror. Examples of a dye having an excitation wavelength different from that of Alexa 488 dye include Alexa 647 dye and Hoechst stains. Alexa 647 dye can be used in labeling the Her2 gene, and Hoechst stains can be used in labeling the nuclei.

Cell detection device 10 may comprise a specimen preparation part for automatically preparing the measurement specimen. In such a case, the specimen preparation part automatically prepares the measurement specimen by admixing the reagents described above into the sample.

Supply flow path 12 connects nozzle 11 and jet nozzle 16. Valves 13, 15 and syringe 14 are arranged in supply flow path 12. The tip of jet nozzle 16 is inserted in inlet 171 of flow cell 17. Syringe 14 is configured such that positive pressure and negative pressure can be applied to supply flow path 12. Driving syringe 14 using negative pressure causes the measurement specimen inside specimen container 10b to be drawn from nozzle 11 and into syringe 14. Driving syringe 14 using positive pressure causes the measurement specimen drawn into syringe 14 to be discharged from jet nozzle 16 and pumped into flow cell 17.

Flow cell 17 comprises inlet 171, disposal outlet 172, and recirculation outlet 173, flow paths 17a, 17b, 17c being provided inside flow cell 17. Flow path 17a is linked to inlet 171, flow path 17b is linked to disposal outlet 172, and flow path 17c is linked to recirculation outlet 173. Flow cell 17 is configured from translucent glass and a synthetic resin. For expediency, FIG. 1 illustrates X-, Y-, and Z-axes that are orthogonal to each other. In flow cell 17, the negative side of the X-axis represents the upstream side of flow cell 17, and the positive side of the X-axis represents the downstream side of flow cell 17. Flow paths 17a, 17b are formed so as to be arranged in a straight line. Flow path 17b is positioned downstream of flow path 17a. Flow path 17c branches from flow path 17a at a position between flow path 17a and flow path 17b. The measurement specimen pumped from jet nozzle 16 flows through flow channel 17a, and then flows through flow channel 17b or flow channel 17c.

Sheath liquid supply part 18 accumulates a sheath liquid, and supplies the sheath liquid to flow path 17a of flow cell 17 through speed-change part 19. Pneumatic pressure source 36 (described later) is connected to sheath liquid supply part 18. Positive pressure is supplied from pneumatic pressure source 36, whereby sheath liquid supply part 18 pumps sheath liquid into speed-change part 19. The measurement specimen pumped from jet nozzle 16 into flow path 17a is caused to flow downstream while enveloped in the sheath liquid. Particles contained in the measurement specimen thereby pass detection position 20a while aligned in a row.

Speed-change part 19 comprises flow paths 19a, 19b, valves 19c, 19d, and orifice 19e. Flow paths 19a, 19b are arranged in parallel in the flow path linking sheath liquid supply part 18 and flow cell 17. Valve 19c is arranged in flow path 19a, and valve 19d and orifice 19e are arranged in flow path 19b. Flow paths 19a, 19b have the same cross-sectional diameter. The cross-sectional diameter of orifice 19e is less than that of flow paths 19a, 19b.

When valve 19c is open and valve 19d is closed, the sheath liquid pumped from sheath liquid supply part 18 is supplied to flow cell 17 through flow path 19a. Conversely, when valve 19c is closed and valve 19d is open, the sheath liquid pumped from sheath liquid supply part 18 is supplied to flow cell 17 through flow path 19b. Due to orifice 19e, V2 is less than V1, where V1 and V2 are defined as the flow volumes per unit time of the sheath liquid supplied to flow cell 17 when the sheath liquid passes through flow paths 19a, 19b, respectively.

As described above, the measurement specimen supplied from jet nozzle 16 to flow path 17a is caused to flow downstream while enveloped in the sheath liquid. Therefore, the measurement specimen flowing through flow path 17a is determined by the flow volume per unit time of the sheath liquid supplied to flow cell 17. Taking the flow volumes per unit time of the sheath liquid supplied to flow cell 17 to be V1, V2 and the speed of the measurement specimen flowing through flow path 17a as a first speed and a second speed, respectively, then because V2 is less than V1, the second speed is lower than the first speed. Thus, by switching the flow volume of the sheath liquid supplied to flow cell 17, it is possible for speed-change part 19 to switch the speed of the measurement specimen flowing through flow path 17a to the first speed or the second speed. The measurement specimen is caused to flow through flow path 17a at the first speed, and the image-capture specimen is caused to flow through flow path 17a at the second speed.

Particle detector 20 detects particles flowing through flow path 17a. Specifically, particle detector 20 irradiates particles positioned at detection position 20a of flow path 17a with light, and detects the resulting fluorescence and forward scattered light. The configuration of particle detector 20 is further described with reference to FIG. 2.

Particle sorter 21 sorts particles that satisfy a test-cell detection condition and other particles on the basis of the result of detection performed by particle detector 20. Measurement specimens containing particles that do not satisfy the test-cell detection condition are sent to waste fluid reservoir part 22 through flow path 17b, and measurement specimens containing particles that satisfy the test-cell detection condition are sent to recirculation flow path 23 through flow path 17c.

Particle sorter 21 comprises member 21a, and a drive part for causing member 21a to project toward flow path 17b. When member 21a is positioned at such a position that flow path 17b is open, the measurement specimen flowing through flow path 17a is sent to waste fluid reservoir part 22 via flow path 17b. Waste fluid reservoir part 22 is linked to disposal outlet 172 of flow cell 17, and accumulates unnecessary measurement specimen. Conversely, when member 21a is positioned at such a position that flow path 17b is blocked, the measurement specimen flowing through flow path 17a is sent to recirculation flow path 23 via flow path 17c. When particles satisfying the test-cell detection condition are positioned at branch position 17d of flow path 17a, particle sorter 21 drives member 21a to block flow path 17b. Particles at branch position 17d are thereby sent to recirculation flow path 23 via flow path 17c.

Particle sorter 21 may comprise a bubble generator instead of the configuration illustrated in FIG. 1. In this case, bubbles produced by the bubble generator of the particle sorter 21 change the advancement direction of the particles flowing in the X-axis positive direction to the direction of flow path 17c. Additionally, particle sorter 21 may comprise a piezo actuator that includes a piezoelectric body and an electrode, or an ultrasonic generator that includes a piezoelectric crystal substrate and a comb electrode, instead of the configuration illustrated in FIG. 1. In this case, particle sorter 21 imparts ultrasonic waves generated by the piezo actuator or ultrasonic generator to the particles, and changes the advancement direction of the particles flowing in the X-axis positive direction to the direction of flow path 17c.

Recirculation flow path 23 connects recirculation outlet 173 of flow cell 17 and supply flow path 12 between valve 13 and syringe 14. Valves 24, 26 and intermediate reservoir part 25 are arranged in recirculation flow path 23. Recirculation flow path 23 allows the measurement specimen that has passed detection position 20a of particle detector 20 to be re-circulated upstream of detection position 20a of flow cell 17, and to flow into flow cell 17 again as an image-capture specimen.

Intermediate reservoir part 25 accumulates the image-capture specimen supplied from flow path 17c to recirculation flow path 23. Intermediate reservoir part 25 is configured such that the accumulated image-capture specimen can be concentrated. Intermediate reservoir part 25 preferably is configured from an elutriator rotor or a centrifuge. A filter, etc., may be used in the concentration of the image-capture specimen.

Intermediate reservoir part 25 may discharge the image-capture specimen, supplied from flow path 17c to recirculation flow path 23, into a reaction tube through a nozzle, and the discharged image-capture specimen may be accumulated in the reaction tube. When the image-capture specimen accumulated in the reaction tube is sent to flow cell 17, intermediate reservoir part 25 draws the image-capture specimen from the reaction tube through a nozzle. The drawn image-capture specimen is then sent to flow cell 17 by syringe 14.

Because the measurement specimen supplied from specimen container 10b to flow cell 17 is mixed with the sheath liquid, the concentration of the image-capture specimen that has been sent to intermediate reservoir part 25 through recirculation flow path 23 decreases. For example, intermediate reservoir part 25 causes the image-capture specimen that had a low concentration to be concentrated to a level comparable to that of the measurement specimen accommodated in specimen container 10b. Thus, according to intermediate reservoir part 25, it is possible to increase the concentration of the image-capture specimen that had been reduced by the sheath liquid. Syringe 14 is driven in a manner similar to the case of the measurement specimen, whereby the image-capture specimen concentrated by intermediate reservoir part 25 is again returned to the same jet nozzle 16, and then pumped from jet nozzle 16 into flow path 17a of flow cell 17.

Particle alignment part 27 comprises piezo actuators 27a, 27b disposed on the side surfaces of flow path 17a. Piezo actuators 27a, 27b include piezoelectric bodies and electrodes. In particle alignment part 27, ultrasonic waves are imparted to the particles flowing through flow path 17a in the Y-axis direction, which is perpendicular to the Z-axis direction that is the direction of image-capture performed by particle-image-capture part 28 and to the X-axis direction that is the direction in which the particles flow, the ultrasonic waves being imparted by piezo actuators 27a, 27b from both sides of flow path 17a. An ultrasonic standing wave is thereby formed between piezo actuators 27a, 27b, as illustrated by dotted lines. Nodes of the ultrasonic standing wave are positioned on the central axis of flow path 17a.

Particles contained in the image-capture specimen that has been re-circulated into flow path 17a through recirculation flow path 23 are aligned so as to flow along the central axis of flow path 17 due to ultrasonic waves being imparted. When the particles are so aligned, the particles accurately pass detection position 20a, which is the position of image-capture performed by particle-image-capture part 28. Accordingly, it is possible for particle-image-capture part 28 to capture images more accurately.

Particle alignment part 27 may be any part capable of forming an ultrasonic standing wave, and may comprise an ultrasonic wave generator that has a piezoelectric crystal substrate and a comb electrode instead of piezo actuators 27a, 27b.

Particle-image-capture part 28 captures an image, at detection position 20a, of a particle in the sorted image-capture specimen supplied to flow cell 17 through recirculation flow path 23. Specifically, particle-image-capture part 28 irradiates the particle positioned at detection position 20a with light, and captures an image of the resulting fluorescence. The configuration of particle-image-capture part 28 is further described with reference to FIG. 2. The entire image-capture specimen that has passed detection position 20a is sent to waste fluid reservoir part 22. The process performed by cell detection device 10 then ends.

In the first embodiment, detection position 20a at which particle detector 20 detects particles and an image-capture position at which particle-image-capture part 28 captures images of the particles coincide in the direction in which the measurement specimen flows in flow path 17a. This makes it possible to reduce the size of flow cell 17. If no size reduction is necessary, particle-image-capture part 28 may capture images of the particles at a position in flow path 17a that is different from detection position 20a. The position at which particle-image-detection part 28 is installed is not provided by way of limitation; particle-image-detection part 28 can be installed downstream of branch position 17d, in flow path 17b or flow path 17c.

Thus, when the particles contained in the measurement specimen first pass detection position 20a, particle detector 20 detects the particles. Only particles that satisfy the test-cell detection condition on the basis of the result of detection performed by particle detector 20 are sent to recirculation flow path 23. Then, when the particles recirculated into flow cell 17 through recirculation flow path 23 pass detection position 20a a second time, particle-image-capture part 28 captures images of the particles. Specifically, detection of the particles occurs in the first round, and image-capture of the particles occurs in the second round. This makes it possible to efficiently acquire cell images.

Figure 2:
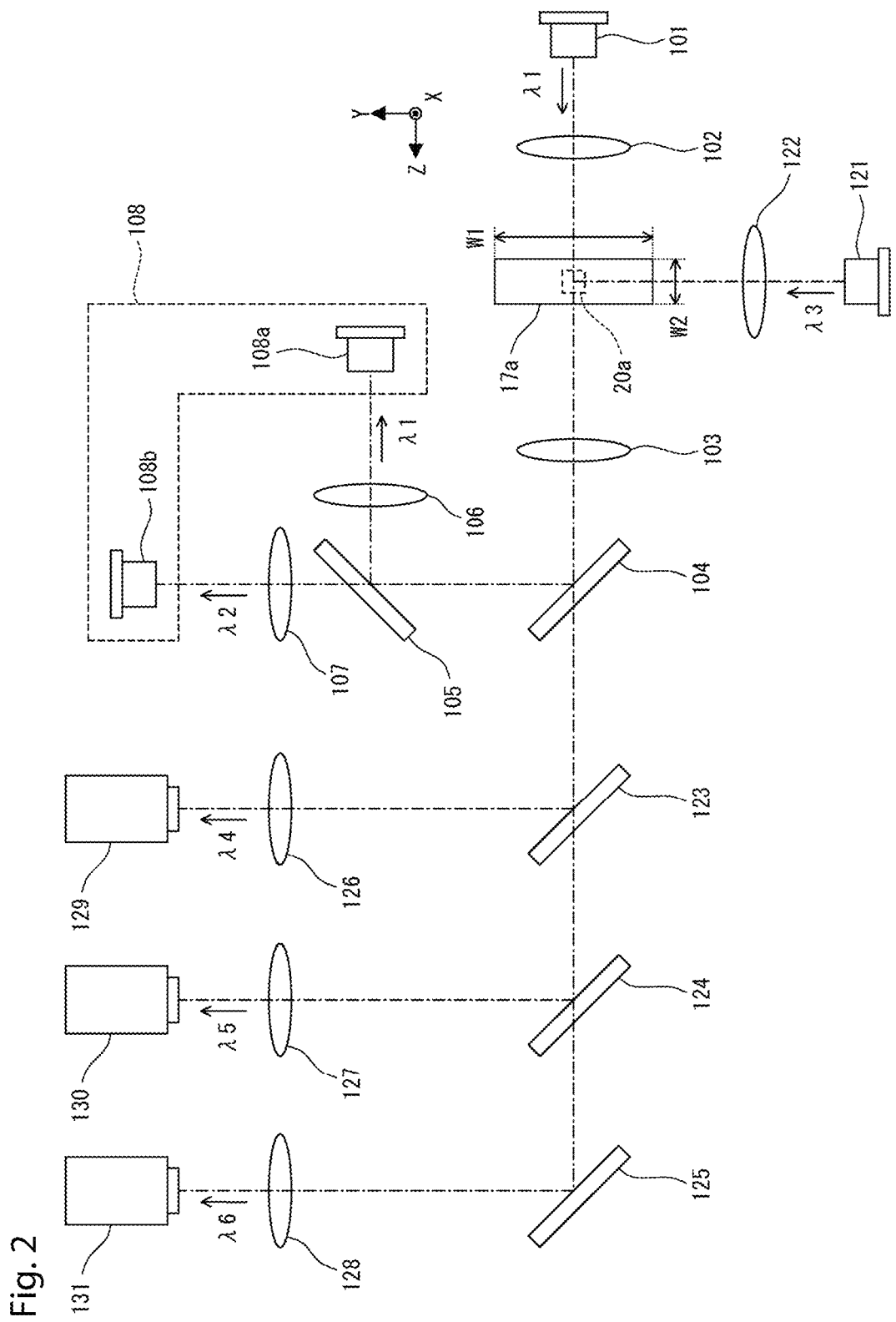
FIG. 2 is a schematic diagram illustrating the configuration of a particle detector and a particle-image-capture part according to the first embodiment.

As illustrated in FIG. 2, particle detector 20 comprises light source 101, irradiation lens 102, objective lens 103, dichroic mirrors 104, 105, condensing lenses 106, 107, and light-reception part 108. Light-reception part 108 comprises first detector 108a and second detector 108b. Particle-image-capture part 28 comprises light source 121, irradiation lens 122, dichroic mirrors 123, 124, 125, condensing lenses 126, 127, 128, and cameras 129, 130, 131.

FIG. 2 illustrates X-, Y-, and Z-axes that correspond to the X-, Y- and Z-axes of FIG. 1. A first direction perpendicular to the direction in which the measurement specimen flows is designated as the Y-axis direction, and a second direction perpendicular to the first direction is designated as the Z-axis direction. Flow path 17a is configured such that first-direction width W1 is greater than second-direction width W2.

Light source 101 is a semiconductor laser light source. The light emitted from light source 101 is laser light of wavelength $\lambda 1$. Wavelength $\lambda 1$ is in the infrared wavelength band. Irradiation lens 102 condenses light emitted from light source 101 and irradiates flow path 17a. The light emitted from light source 101 impinges on flow path 17a from the second direction; i.e., from the Z-axis direction. The particle positioned at detection position 20a is irradiated with the light of wavelength $\lambda 1$ that impinges on flow path 17a, whereby forward scattered light of wavelength $\lambda 1$ is produced from the particle and fluorescence of wavelength $\lambda 2$ is produced from the CD45 labeled antibodies.

Objective lens 103 condenses the forward scattered light of wavelength $\lambda 1$ and the fluorescence of wavelength $\lambda 2$, and then condenses fluorescence of wavelengths $\lambda 4$, $\lambda 5$, and $\lambda 6$ (described later). Dichroic mirror 104 reflects the forward scattered light of wavelength $\lambda 1$ and the fluorescence of wavelength $\lambda 2$, and transmits the fluorescence of wavelengths $\lambda 4$, $\lambda 5$, and $\lambda 6$. Dichroic mirror 105 reflects the forward scattered light of wavelength $\lambda 1$, and transmits the fluorescence of wavelength $\lambda 2$. Condensing lens 106 condenses the forward scattered light of wavelength $\lambda 1$. First detector 108a receives the forward scattered light of wavelength $\lambda 1$. First detector 108a is a photodiode, outputting an electrical signal corresponding to the intensity of the received forward scattered light. Condensing lens 107 condenses the fluorescence of wavelength $\lambda 2$. Second detector 108b receives the fluorescence of wavelength $\lambda 2$. Second detector 108b is an avalanche photodiode, outputting an electrical signal corresponding to the intensity of the received fluorescence.

Light source 121 is a semiconductor laser light source. The light emitted from light source 121 is laser light of wavelength $\lambda 3$. Wavelength $\lambda 3$ is approximately 488 nm. Irradiation lens 122 condenses light emitted from light source 121 and irradiates flow path 17a. The light emitted from light source 121 impinges on flow path 17a from the first direction; i.e., from the Y-axis direction. The particle positioned at detection position 20a is irradiated with the light of wavelength $\lambda 3$ that impinges on flow path 17a, whereby fluorescence of wavelength $\lambda 4$ is produced from the Alexa 488 dye, fluorescence of wavelength $\lambda 5$ is produced from the PE dye, and fluorescence of wavelength $\lambda 6$ is produced from the 7AAD dye.

Thus, when fluorescence excitation light emitted from light source 121 impinges on flow path 17a from the first direction, fluorescence can be efficiently produced. Specifically, the particles flowing through flow path 17a are less likely to move in an irregular manner in the short-side direction. Therefore, in cases where fluorescence excitation light impinges from the short side of flow path 17a, particles at detection position 20a can be irradiated with fluorescence excitation light even when the fluorescence excitation light beam is thin. Accordingly, because the particles can be efficiently irradiated with fluorescence excitation light, fluorescence can be efficiently produced.

Objective lens 103 condenses the fluorescence of wavelengths $\lambda 4$, $\lambda 5$, and $\lambda 6$. In FIG. 2, particle-image-capture part 28 shares use of the objective lens 103 with particle detector 20. The fluorescence of wavelengths $\lambda 4$, $\lambda 5$, and $\lambda 6$ condensed by objective lens 103 passes through dichroic mirror 104. Dichroic mirror 123 reflects the fluorescence of wavelength $\lambda 4$, and transmits the fluorescence of wavelengths $\lambda 5$ and $\lambda 6$. Dichroic mirror 124 reflects the fluorescence of wavelength $\lambda 5$, and transmits the fluorescence of wavelength $\lambda 6$. Dichroic mirror 125 reflects fluorescence of wavelength $\lambda 6$. Dichroic mirror 125 may be replaced with a reflective mirror.

Condensing lenses 126, 127, 128 condense the fluorescence of wavelengths $\lambda 4$, $\lambda 5$, and $\lambda 6$, respectively. Cameras 129, 130, 131 receive the fluorescence of wavelengths $\lambda 4$, $\lambda 5$, and $\lambda 6$, respectively, and output image information about the particle positioned at detection position 20a as an image-capture signal. Cameras 129, 130, 131 may be time-delay integration (TDI) cameras. When TDI cameras are used, more accurate image information can be acquired.

The direction in which cameras 129, 130, 131 capture images of the particle is the Z-axis direction. As described above, flow path 17a is configured such that width W1 in the Y-axis direction, which is the direction perpendicular to the image-capture direction and to the direction in which the particles flow, is greater than width W2 in the Z-axis direction, which is the image-capture direction. Accordingly, because the Z-axis-direction position of the particles does not tend to vary, the particles readily come into focus even when the image-capture magnification is increased and the depth of field is narrowed. Accordingly, particle images can be accurately acquired.

Figure 3:
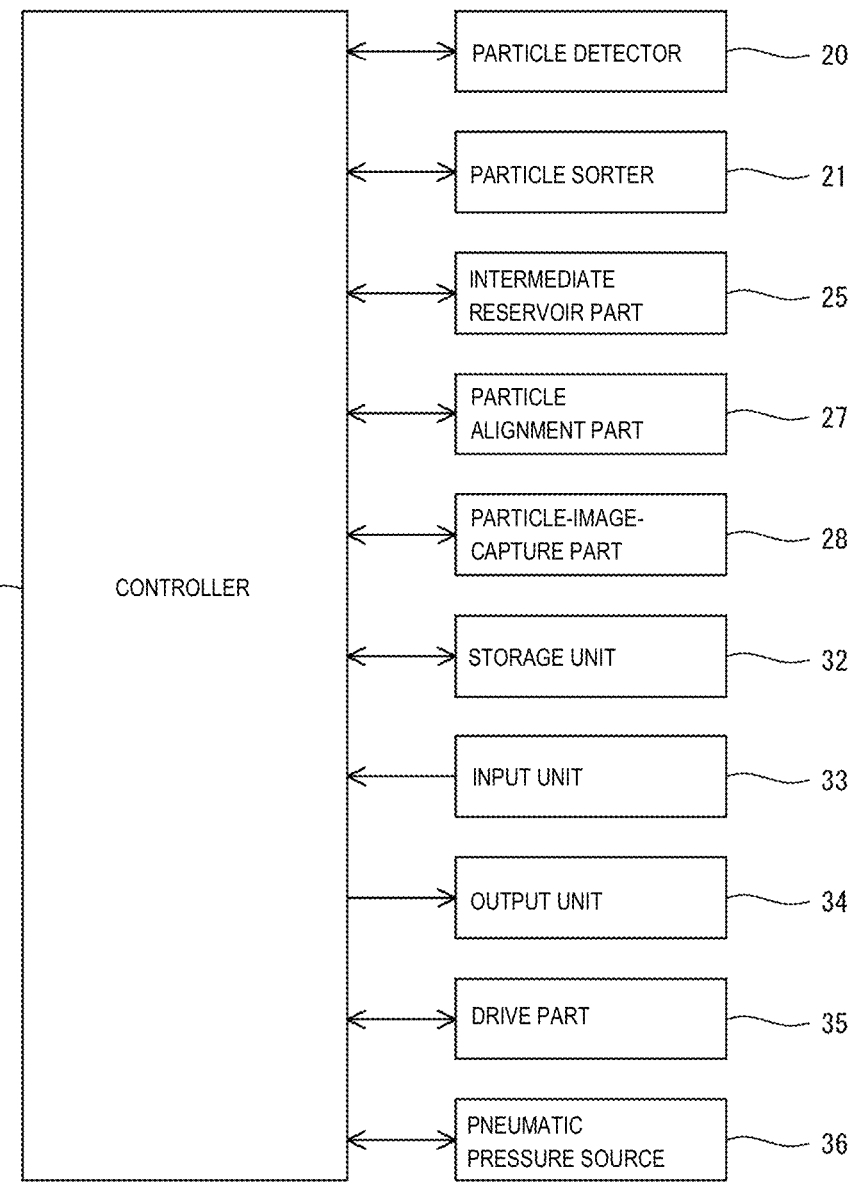
FIG. 3 is a block diagram illustrating the configuration of the cell detection device according to the first embodiment.

As illustrated in FIG. 3, cell detection device 10 comprises particle detector 20 illustrated in FIG. 1, particle sorter 21, intermediate reservoir part 25, particle alignment part 27, and particle-image-capture part 28. Furthermore, cell detection device 10 comprises controller 31, storage unit 32, input unit 33, output unit 34, drive unit 35, and pneumatic pressure source 36. Controller 31 is, e.g., a CPU. Controller 31 receives signals from each of the parts of cell detection device 10, and controls each of the parts of cell detection device 10. Controller 31 controls each of the parts in accordance with a program stored in storage unit 32. Storage unit 32 is ROM, RAM, a hard disk, or the like.

Controller 31 acquires peak values of the signal waveforms outputted by first detector 108a and second detector 108b of particle detection unit 20, whereby the intensity of the forward scattered light of wavelength λ1 and the intensity of the fluorescence of wavelength λ2 are acquired for each of the particles. Controller 31 stores the intensity of the forward scattered light of wavelength λ1 and the intensity of the fluorescence of wavelength λ2 in storage unit 132 for each of the particles. Controller 31 generates images of the particles on the basis of the signals outputted from cameras 129, 130, 131 of particle-image-capture part 28, and stores the produced images in storage unit 32 for each of the particles.

Controller 31 receives a command from an operator via input unit 33, and causes output unit 34 to display, inter alia, the images of the particles. Input unit 33 includes a mouse and a keyboard, and output unit 34 includes a display comprising a liquid crystal panel, etc.

Drive unit 35 includes a mechanism for individually driving the valves illustrated in FIG. 1, a mechanism for driving syringe 14, and a mechanism for raising and lowering nozzle 11. Pneumatic pressure source 36 supplies positive pressure and negative pressure to each of the parts of cell detection device 10.

The processes performed by cell detection device 10 are described below with reference to the flowcharts illustrated in FIG. 4 through FIG. 6A.

Figure 4:
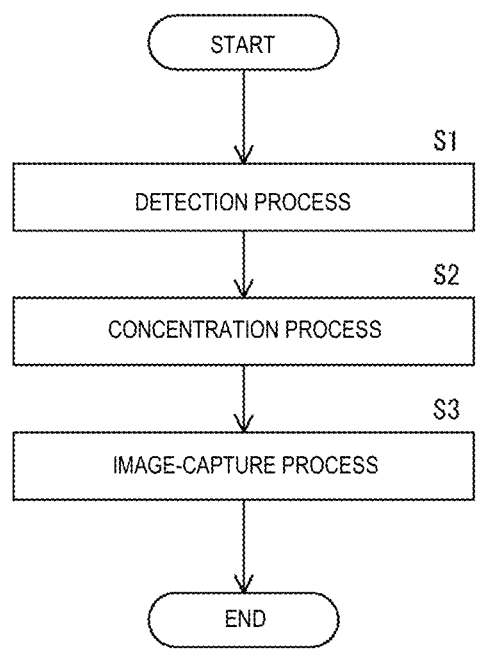
FIG. 4 is a flowchart illustrating the processes performed by the cell detection device according to the first embodiment.

As illustrated in FIG. 4, when a start command is inputted by an operator, controller 31 performs a detection process in step S1. Specifically, controller 31 starts the processes illustrated in FIG. 5A and FIG. 5B (described later) in parallel, whereby the measurement specimen in specimen container 10b is supplied to flow cell 17, and particle detector 20 detects the particles contained in the measurement specimen. Only particles satisfying the test-cell detection condition are supplied to recirculation flow path 23. When the processes in FIG. 5A and FIG. 5B end, controller 31 advances the process to step S2.

In step S2, controller 31 performs a concentration process. The image-capture specimen accumulated in intermediate reservoir part 25 is thereby concentrated. Intermediate reservoir part 25 accumulates the concentrated image-capture specimen.

In step S3, controller 31 performs an image-capture process. Specifically, controller 31 starts the process illustrated in FIG. 6A (described later). The image-capture specimen that has been concentrated by intermediate reservoir part 25 is thereby resupplied to flow cell 17. Particle-image-capture part 28 captures images of the particles contained in the image-capture specimen that has been resupplied to flow cell 17. When the process illustrated in FIG. 6A ends, and the entire image-capture specimen that has been re-circulated into flow cell 17 is sent to waste fluid reservoir part 22, the processes performed by cell detection device 10 as illustrated in FIG. 4 end.

Figure 5A:
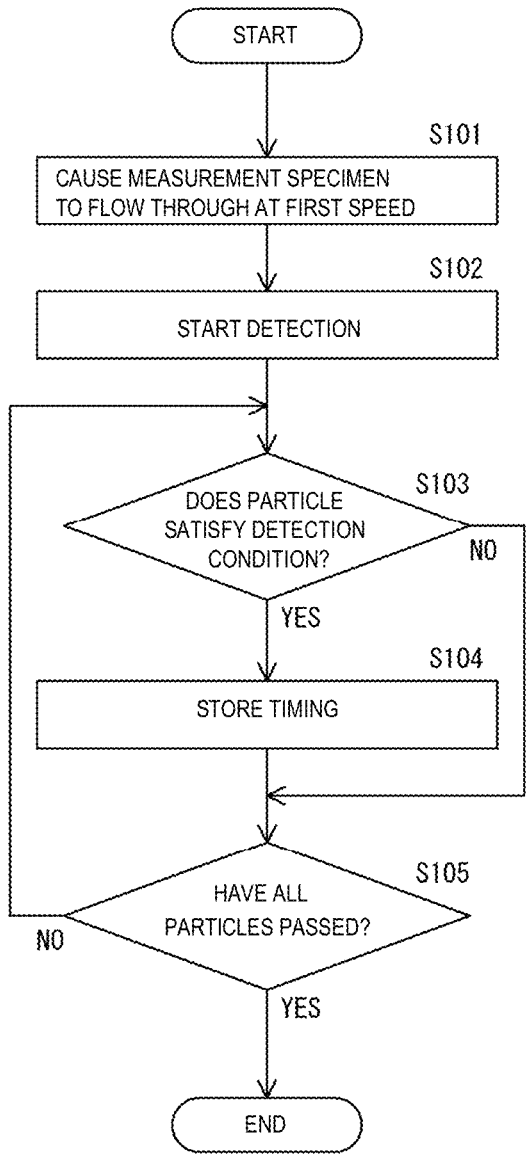
FIG. 5A and FIG. 5B are flowcharts illustrating the processes initiated by a detection process according to the first embodiment.

As illustrated in FIG. 5A, in step S101, controller 31 causes the measurement specimen to flow into flow cell 17 at the first speed. Specifically, controller 31 opens valve 19c and closes valve 19d, and supplies the sheath liquid from sheath liquid supply part 18 to flow cell 17. Controller 31 then pumps the measurement specimen inside specimen container 10b from jet nozzle 16 into flow path 17a.

In step S102, controller 31 starts detection by particle detection unit 20. Specifically, controller 31 irradiates detection position 20a with light from light source 101, and receives forward scattered light at wavelength λ1 and fluorescence at wavelength λ2 using first detector 108a and second detector 108b, respectively. Controller 31 receives the intensity of the forward scattered light at wavelength λ1 and the intensity of the fluorescence at wavelength λ2 from the particle at detection position 20a.

In step S103, controller 31 assesses whether the particle at detection position 20a satisfies the test-cell detection condition. Specifically, when the intensity of the fluorescence at wavelength λ2 is equal to or less than a prescribed threshold value, and the intensity of the forward scattered light at wavelength λ1 is equal to or greater than a prescribed threshold value, controller 31 assesses that the particle at detection position 20a satisfies the test-cell detection condition. Particles in which the intensity of the fluorescence at wavelength λ2 is greater than the prescribed threshold value and particles in which the intensity of the forward scattered light at wavelength λ1 is less than the prescribed threshold value are thereby excluded. Because particles that are test-cell CTCs do not bond to the CD45 labeled antibodies, the intensity of the fluorescence at wavelength λ2 is equal to or less than the prescribed threshold value. Additionally, because particles that are test-cell CTCs are of large size, the intensity of the forward scattered light at wavelength λ1 is equal to or greater than the prescribed threshold value.

Thus, in cases where the detected particles are particles other than white blood cells, and in cases where the detected particles are large, controller 31 assesses there to be a strong possibility that the detected particles are test cells ("YES" in step S103).

The hemolytic agents for causing hemolysis of red blood cells do not have to be used in the preparation of the measurement specimen. Even so, red blood cells in the measurement specimen are excluded because they are small and the intensity of the forward scattered light of wavelength λ1 is less than the prescribed threshold value.

When an assessment of "YES" is obtained in step S103, then in step S104 controller 31 stores the timing at which the particles that were assessed in step S103 to satisfy the test-cell detection condition pass detection position 20a. In step S105, controller 31 assesses whether the entire measurement specimen inside specimen container 10b has been supplied to flow cell 17, and whether all of the particles have passed detection position 20a. Controller 31 repeats the processes in steps S103 and S104 until all of the particles have passed detection position 20a. When all of the particles have passed detection position 20a, the process in FIG. 5A ends.

Figure 5B:
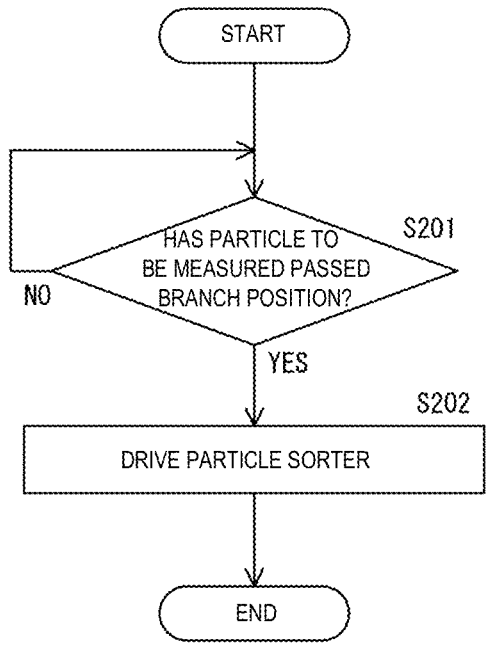

As illustrated in FIG. 5B, in step S201, controller 31 assesses whether the particles to be re-circulated have reached branch position 17d. Specifically, when a prescribed period of time has elapsed after the timing stored in step S104 of FIG. 5A, controller 31 assesses that the particles that were assessed in step S103 of FIG. 5A to satisfy the test-cell detection condition have reached branch position 17d.

In step S202, when the particles to be re-circulated have reached branch position 17d, controller 31 drives particle sorter 21 so that member 21 blocks flow path 17b for a prescribed period of time. The particles satisfying the test-cell-detection condition are thereby sent to recirculation flow path 23 via flow path 17c. After the process in FIG. 5A ends, the process in FIG. 5B is repeated until a prescribed period of time elapses. All of the test-cell-detection-condition-satisfying particles contained in the measurement specimen are then sent to recirculation flow path 23.

In cases where particles that do not satisfy the test-cell detection condition pass branch position 17d, flow path 17c may be blocked. In such a case, particle sorter 21 comprises a member that blocks flow path 17c. In step S202, controller 31 blocks flow path 17c using the member that blocks flow path 17c, and retracts member 21a from flow path 17b.

As illustrated in FIG. 6A, in step S301, controller 31 causes the image-capture specimen concentrated by intermediate reservoir part 25 to flow into flow cell 17 at the second speed, which is lower than the first speed. Specifically, controller 31 closes valve 19c and opens valve 19d, and supplies the sheath liquid from sheath liquid supply part 18 to flow cell 17. Controller 31 then pumps the image-capture specimen concentrated by intermediate reservoir part 25 from jet nozzle 16 into flow path 17a.

In step S302, controller 31 drives particle alignment part 27 and imparts ultrasonic waves to flow path 17a. The particles flowing through flow path 17a thereby flow along the central axis of flow path 17a. In step S303, controller 31 starts detection by particle detection unit 20, similarly to step S102 of FIG. 5A.

The process in FIG. 5A differs from the process in FIG. 6A in that particle alignment part 27 is not driven in the process in FIG. 5A, since the particles contained in the measurement specimen are readily positioned along the central axis of flow path 17a when the specimen is caused to flow through flow path 17a at the first speed, even if particle alignment part 27 is not driven. However, because the image-capture specimen being re-circulated is caused to flow through flow path 17a at the second speed, which is lower than the first speed, the particles might move in an irregular manner. Accordingly, particle alignment part 27 is driven in the process in FIG. 6A.

In step S304, controller 31 assesses whether a particle is positioned at detection position 20a on the basis of the intensity of the forward scattered light received by first detector 108a. Specifically, when the intensity of the forward scattered light exceeds the prescribed threshold value, controller 31 assesses that a particle is positioned at detection position 20a. In step S305, when a particle is positioned at detection position 20a, controller 31 captures an image of the particle positioned at detection position 20a using particle-image-capture part 28. Specifically, controller 31 irradiates detection position 20a with light from light source 121, and receives the fluorescence at wavelengths λ4, λ5, and λ6 using cameras 129, 130, 131, respectively. Controller 31 generates an image of the particle on the basis of image-capture signals outputted by cameras 129, 130, 131. In step S105, cameras 129, 130, 131 may capture images, or video.

In step S306, controller 31 assesses whether the entire image-capture specimen concentrated by intermediate reservoir part 25 has been supplied to flow cell 17, and whether all of the particles have passed detection position 20a. Controller 31 repeats the processes in steps S304 and S305 until all of the particles have passed detection position 20a. When all of the particles have passed detection position 20a, the process in FIG. 6A ends. Images are then acquired for all of the particles contained in the image-capture specimen re-circulated into flow cell 17.

Thus, since the first round involves assessing whether the particles are highly likely to be CTCs and the second round involves capturing images of the particles, it is possible to set the speed of the measurement specimen in the first round higher than that of the image-capture specimen in the second round using speed-change part 19. Accordingly, the throughput of the processes performed by cell detection device 10 can be increased.

When the processes in FIG. 4 through FIG. 6A end, an operator inputs a results-display command to cell detection device 10 via input unit 33.

As illustrated in FIG. 6B, in step S401, controller 31 assesses whether a results-display command has been inputted by the operator. When an assessment of "YES" is obtained in step S401, then in step S402 controller 31 analyzes all of the particle images acquired in step S305 of FIG. 5A, and extracts cells in which the nucleus includes a luminescent point based on chromosome 17 and a luminescent point based on the Her2 gene. Furthermore, in step S402, controller 31 analyzes the images of the extracted cells, assesses for each of the cells whether the Her2 gene is amplified, and extracts cells in which the Her2 gene is amplified as CTCs. Controller 31 extracts cells in which the nucleus includes two luminescent points based on chromosome 17 and three or more luminescent points based on the Her2 gene as cells in which the Her2 gene is amplified; i.e., as CTCs.

In step S403, controller 31 displays the number of cells that include luminescent points, and the number of cells in which the Her2 gene is amplified (CTCs), on output unit 34 on the basis of the result of extraction performed in step S402. In step S404, controller 31 displays the images of the cells that include luminescent points as extracted in step S402 on output unit 34.

Figure 7A:
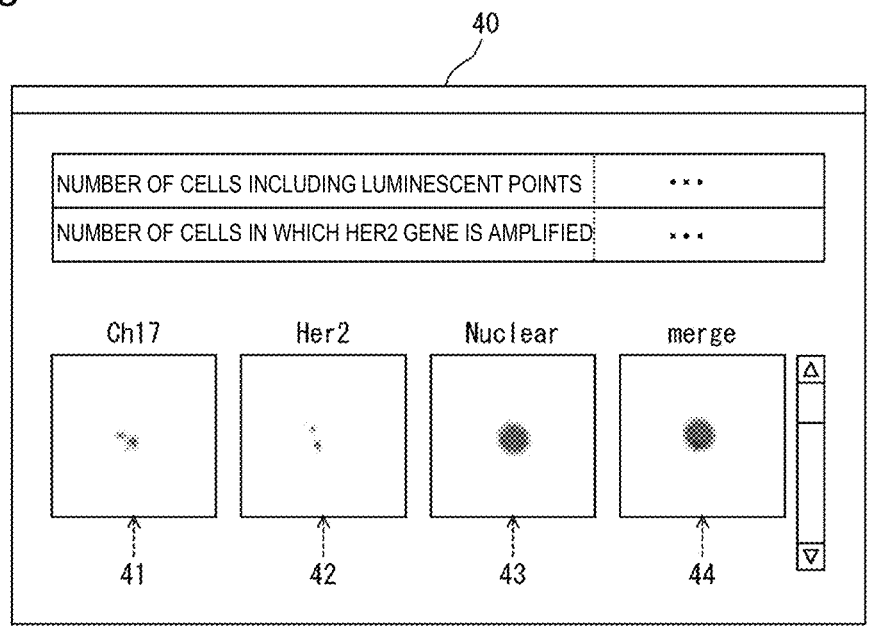
FIG. 7A and FIG. 7B are diagrams illustrating screens displayed by an output unit according to the first embodiment.
Figure 7B:
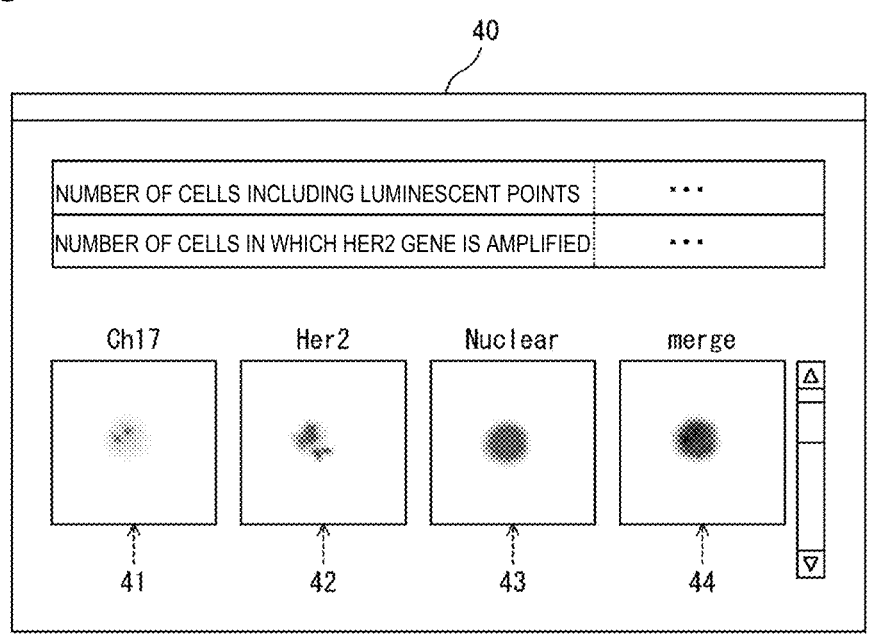

As illustrated in FIG. 7A and FIG. 7B, in steps S403 and S404, output unit 34 displays screens 40. Screens 40 display the number of cells that include luminescent points, the number of cells in which the Her2 gene is amplified (CTCs), and the images of the cells that include luminescent points. Since, by referring to the numbers of cells, the operator can know whether amplification of the Her2 gene is occurring, it is possible to provide information that is useful for a physician, etc., to determine optimal therapeutic agents.

The four images arranged in the horizontal direction are images of the same particle. The four images, in order from the left, respectively illustrate image 41 of the fluorescence produced by the dye that labels genes in chromosome 17, image 42 of the fluorescence produced by the dye that labels the Her2 gene, image 43 of the fluorescence produced by the dye that stains nuclei, and image 44 formed by merging images 41-43. Images 41-44 are inverted in tone, and then converted to grayscale.

The particle images illustrated in FIG. 7A are of cells in which the Her2 gene is not amplified, and the particle images illustrated in FIG. 7B are of breast-cancer cells in which the Her2 gene is amplified. When there are multiple particle images that include luminescent points, the operator can switch between and display particle images on screen 40. Furthermore, screen 40 may separately be provided with a button, etc., with which it is possible to individually display images of cells in which the Her2 gene is amplified and images of cells in which the Her2 gene is not amplified.

The number of luminescent points in image 41 represents the number of genes in chromosome 17. The number of luminescent points in image 42 represents the number of Her2 genes. The luminescent point in image 43 represents the nucleus. This makes it possible for the operator, by referring to the images, to actually know whether genes in chromosome 17 and the Her2 gene are present in the nucleus. If the Her2 gene is not amplified, there are two luminescent points in images 41, 42, as illustrated in FIG. 7A; if the Her2 gene is amplified, there are two luminescent points in image 41 and more than two luminescent points in image 42, as illustrated in FIG. 7B. This makes it possible for the operator, by referring to the images, to actually know whether amplification of the Her2 gene is occurring.

Antibodies that are specific to EpCAM antigens expressed in CTCs and that bond to magnetic fluid particles make it possible to magnetically label CTCs that express EpCAM antigens. When CTCs are magnetically labeled in this manner, a magnetic field gradient is applied to the chamber in which the measurement specimen is accommodated. Once this is done, the magnetically labeled CTCs are aligned on an observation surface of the chamber; therefore, observing the observation surface makes it possible to detect the presence of CTCs. However, there are cases where CTCs do not express EpCAM antigens, and CTCs that do not express EpCAM antigens might be overlooked by this method. According to the first embodiment, an assessment is made as to whether the Her2 gene is amplified on the basis of images captured by particle-image-capture part 28, and then an assessment is made as to whether CTCs are present. Accordingly, according to the first embodiment, it is possible to reduce the chance that CTCs might be overlooked.

Second Embodiment

As illustrated in FIG. 8, in the second embodiment, contrasted with the first embodiment, particle-image-capture part 28 is further provided with condensing lens 141 and camera 142, and the functions of dichroic mirrors 104, 123-125 are changed. The configuration of cell detection device 10 is otherwise the same as in the first embodiment.

Dichroic mirror 104 in the second embodiment reflects half of the forward scattered light of wavelength $\lambda 1$, and transmits the other half. Of the forward scattered light of wavelength $\lambda 1$ produced by the particle at detection position 20a, half is reflected by dichroic mirror 104; the other half is transmitted by dichroic mirror 104, and is furthermore transmitted by dichroic mirrors 123-125. Condensing lens 141 condenses the forward scattered light of wavelength $\lambda 1$. Camera 142 receives the forward scattered light of wavelength $\lambda 1$, and outputs image information about the particle positioned at detection position 20a as an image-capture signal. When the image-capture specimen is re-circulated from recirculation flow path 23 into flow cell 17, controller 31 assesses whether a particle is positioned at detection position 20a on the basis of the intensity of the forward scattered light received by first detector 108, and generates a bright-field image on the basis of the image-capture signal outputted by camera 142.

Figure 9A:
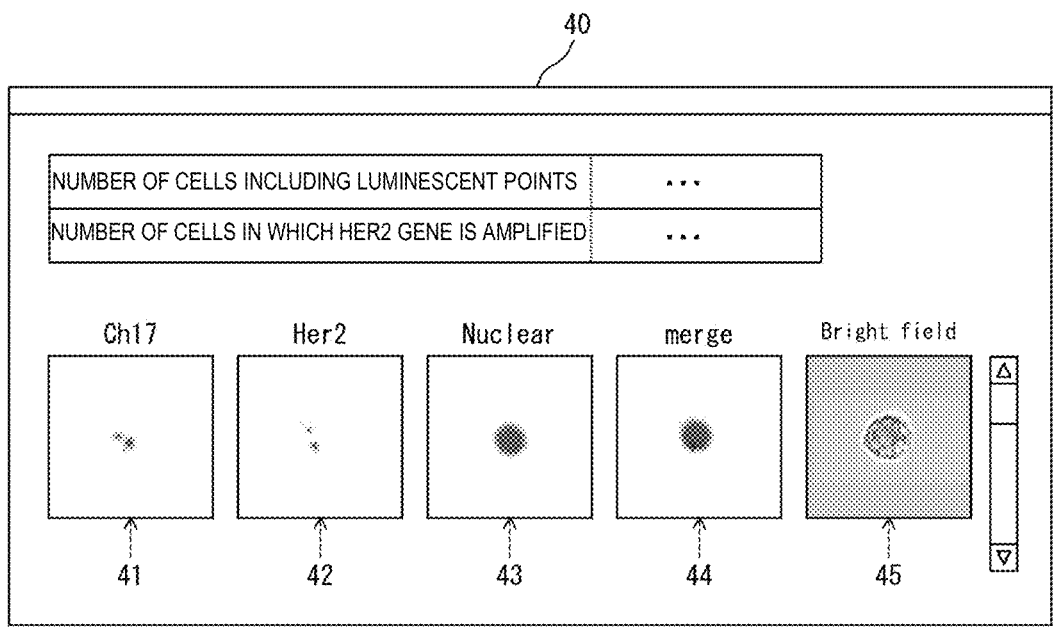
FIG. 9A and FIG. 9B are diagrams illustrating screens displayed by an output unit according to the second embodiment.
Figure 9B:
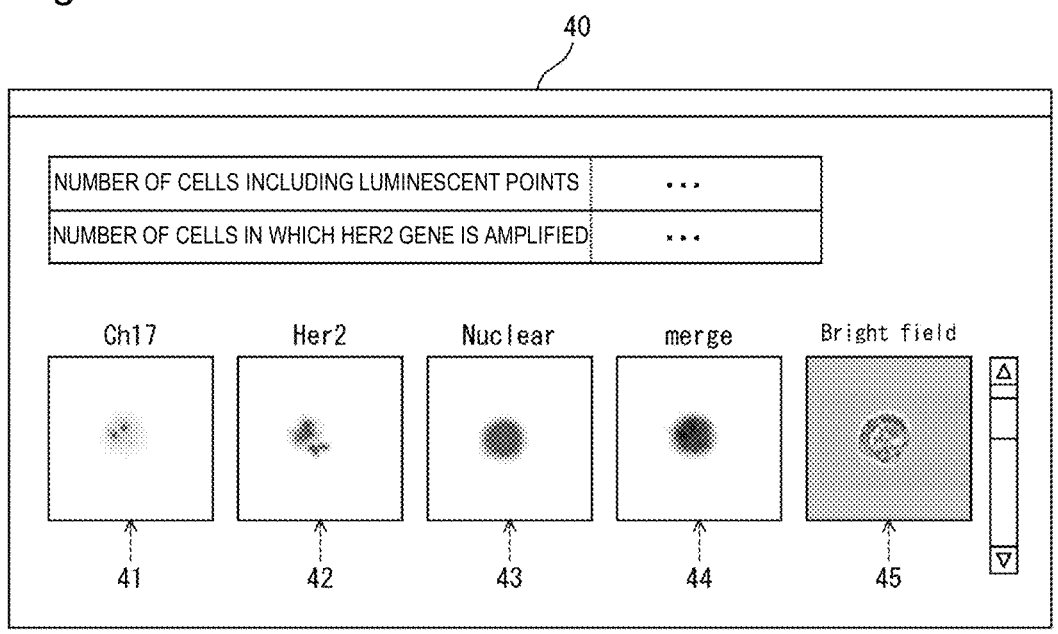

In the second embodiment, in steps S403 and S404 of FIG. 6B, screens 40 illustrated in FIG. 9A and FIG. 9B are displayed by output unit 34. Screens 40 illustrated in FIG. 9A and FIG. 9B illustrate bright-field image 45 in addition to images 41-44 illustrated in FIG. 7A and FIG. 7B. In the second embodiment, the operator can refer to image 45 in conjunction with images 41-44 to confirm the cell type, etc.

Third Embodiment

Figure 10:
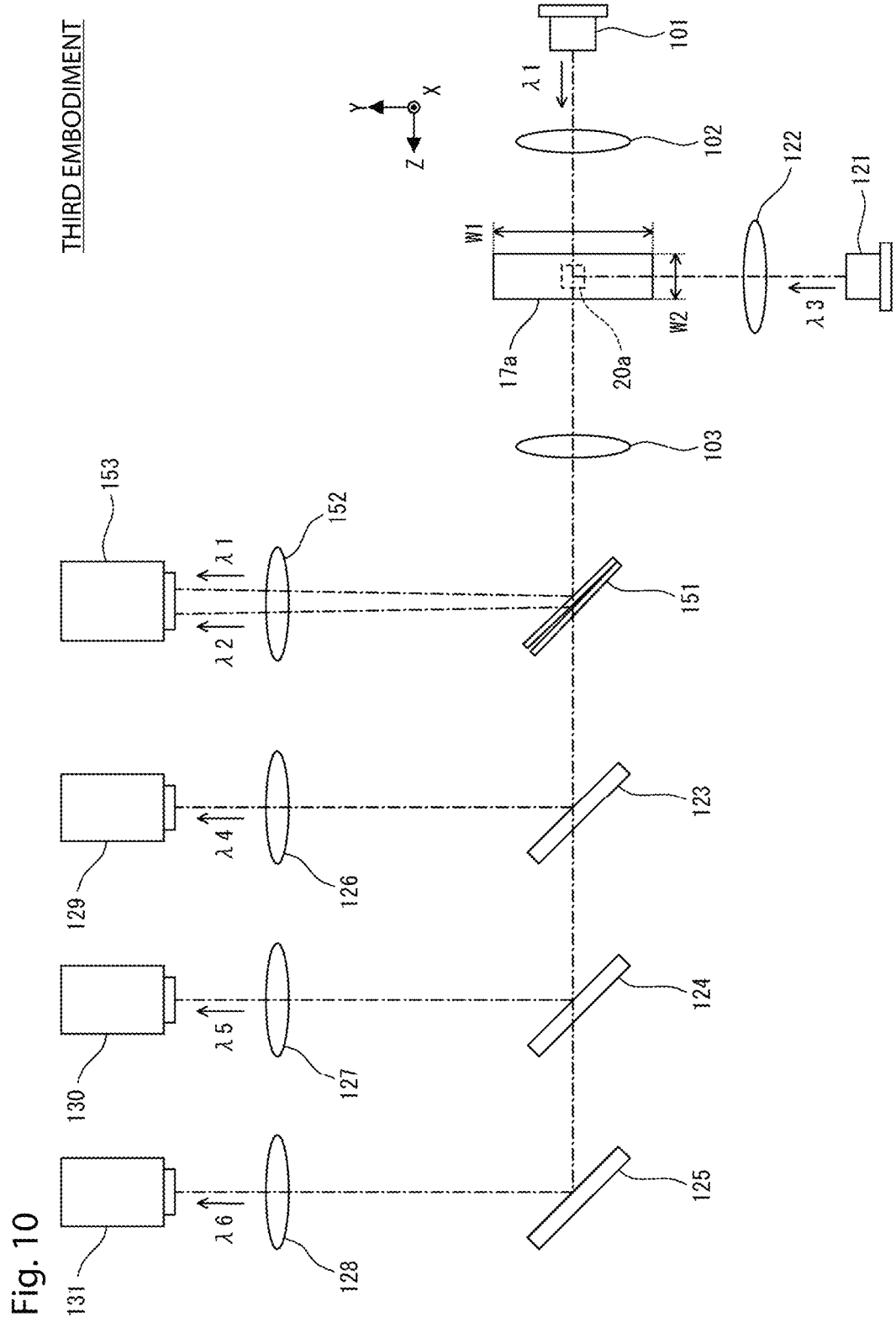
FIG. 10 is a schematic diagram illustrating the configuration of a particle detector and a particle-image-capture part according to a third embodiment.

As illustrated in FIG. 10, in the third embodiment, the configuration of particle detector 20 is different from that in the first embodiment. In the third embodiment, optical unit 151, condensing lens 152, and camera 153 are used as the configuration that detects forward scattered light of wavelength $\lambda 1$ and fluorescence of wavelength $\lambda 2$. The configuration of cell detection device 10 is otherwise the same as in the first embodiment.

Optical unit 151 has a configuration in which two dichroic mirrors are combined. The two dichroic mirrors of optical unit 151 reflect forward scattered light of wavelength $\lambda 1$ and fluorescence of wavelength $\lambda 2$ at angles that are slightly different from each other, causing the light and the fluorescence to be separated on light-reception surface 153a of camera 153 (described later). Optical unit 151 transmits fluorescence of wavelengths $\lambda 4$, $\lambda 5$, and $\lambda 6$. Condensing lens 152 condenses the forward scattered light of wavelength $\lambda 1$ and the fluorescence of wavelength $\lambda 2$. Camera 153 receives the forward scattered light of wavelength $\lambda 1$ and the fluorescence of wavelength $\lambda 2$, and outputs image information about the particle positioned at detection position 20a as an image-capture signal.

Figure 11:
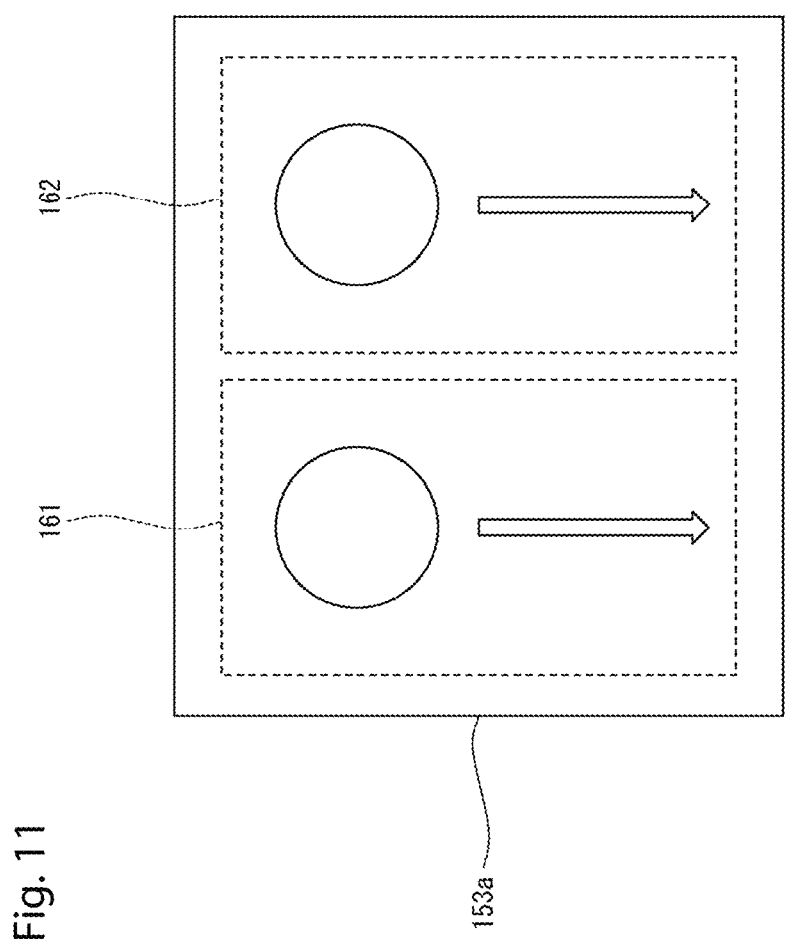
FIG. 11 is a schematic diagram illustrating regions on a light-reception surface of a camera according to the third embodiment.

As illustrated in FIG. 11, camera 153 receives the forward scattered light of wavelength $\lambda 1$ and the fluorescence of wavelength $\lambda 2$ in regions 161, 162 of light-reception surface 153a, respectively. Light-reception surface 153a is a light-receiving surface of a CMOS image sensor or another such image-capture element disposed in camera 153. As the particles move through flow path 17a, the positions of light irradiated on light-reception surface 153a move within regions 161, 162, respectively, as illustrated by arrows. Thus, since the two types of light are separated on light-reception surface 153a by optical unit 151, controller 31 can extract signals corresponding to each of the types of light from the image-capture signal outputted by camera 153.

When the intensity of the forward scattered light of wavelength $\lambda 1$ and the intensity of the fluorescence of wavelength $\lambda 2$ are acquired, controller 31 acquires the intensity of the forward scattered light of wavelength $\lambda 1$ by adding the signals outputted from region 161, and acquires the intensity of the fluorescence of wavelength $\lambda 2$ by adding the signals outputted from region 162. Controller 31 refers to the acquired intensities when detecting particles in step S103 of FIG. 5A. When particle images are acquired, controller 31 acquires the intensity of the forward scattered light in the same manner as that described above, and refers to the acquired intensity when assessing whether a particle is positioned at detection position 20a in step S304 of FIG. 6A. At this time, controller 31 simultaneously processes the image-capture signal from region 161 and generates a bright-field image of the particle. Controller 31 displays the generated bright-field image in the same manner as in FIG. 9A and FIG. 9B.

When the bright-field image is displayed on output unit 34, the operator can refer to the bright-field image in conjunction with the other images to confirm the cell type, etc., in the same manner as in the second embodiment.

Particle detector 20 may comprise cameras that individually and respectively receive the forward scattered light of wavelength λ1 and the fluorescence of wavelength λ2 instead of camera 153.

Fourth Embodiment

As illustrated in FIG. 12, in the fourth embodiment, contrasted with the third embodiment, dichroic mirrors 123-125, condensing lenses 126-128, and cameras 129-131 are omitted, and the configuration of optical element 151 is changed. Regions 163, 164, 165 (described later) are added to light-reception surface of camera 153. The configuration of cell detection device 10 is otherwise the same as in the third embodiment.

Optical unit 151 has a configuration in which five dichroic mirrors are combined. The five dichroic mirrors of optical unit 151 reflect forward scattered light of wavelength λ1 and fluorescence of wavelengths λ2, λ4-λ6 at angles that are slightly different from each other, causing the light and the fluorescence to be separated on light-reception surface 153a of camera 153. Condensing lens 152 condenses the forward scattered light of wavelength λ1 and the fluorescence of wavelengths λ2, λ4-λ6. Camera 153 receives the forward scattered light of wavelength λ1 and the fluorescence of wavelengths λ2, λ4-λ6, and outputs image information about the particle positioned at detection position 20a as an image-capture signal.

Figure 13:
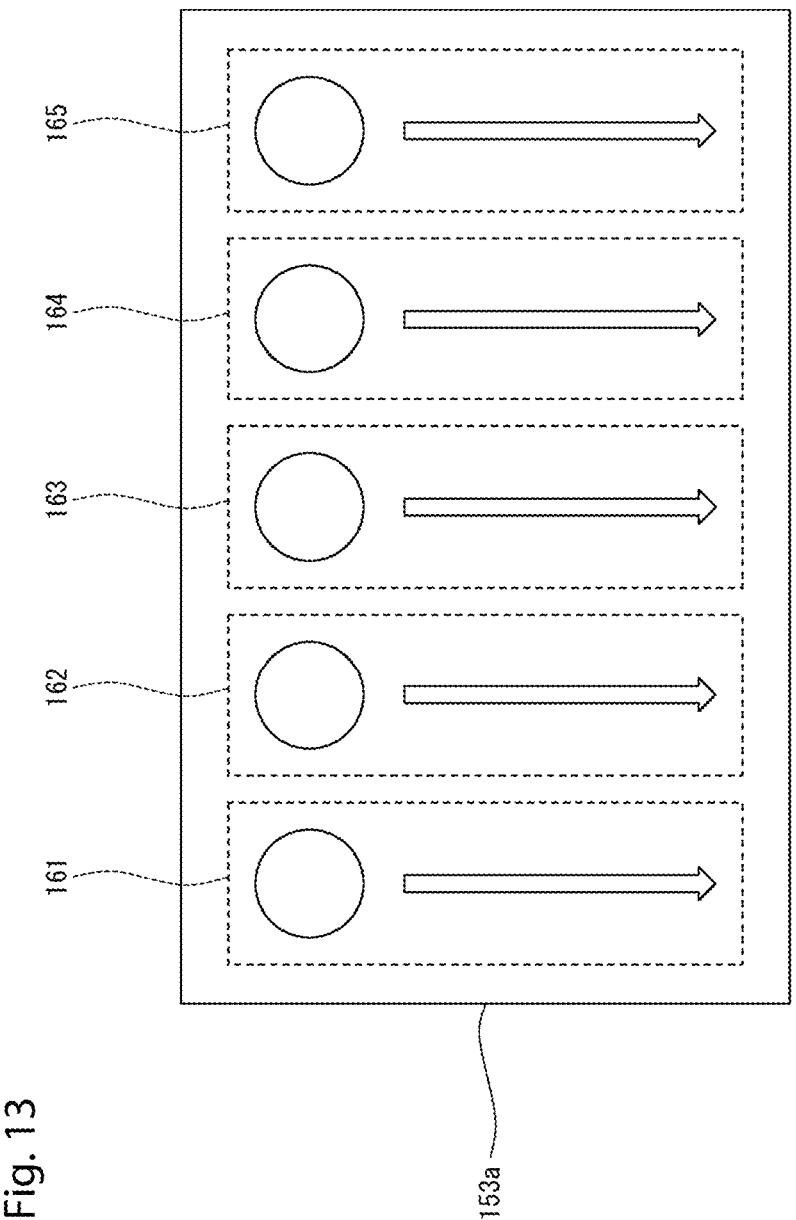
FIG. 13 is a schematic diagram illustrating regions on a light-reception surface of a camera according to the fourth embodiment.

As illustrated in FIG. 13, camera 153 receives the forward scattered light of wavelength λ1 and the fluorescence of wavelength λ2, λ4-λ6 in regions 161-165 of light-reception surface 153a, respectively. Thus, since the five types of light are separated on light-reception surface 153a by optical unit 151, controller 31 can extract signals corresponding to each of the types of light from the image-capture signal outputted by camera 153. The process based on the signals from regions 161, 162 is the same as in the third embodiment. When it is assessed that a particle is present at detection position 20a in a case where the image-capture specimen is re-circulated from recirculation flow path 23 into flow cell 17, controller 31 generates a bright-field image corresponding to the forward scattered light irradiated on region 161, and images corresponding to the fluorescence irradiated on regions 163-163, on the basis of the image-capture signal outputted by camera 153.

In the fourth embodiment, contrasted with the third embodiment, cameras 129-131 of particle-image-capture part 28 are omitted, and particle-image-capture part 28 shares use of camera 153 with particle detector 20. Accordingly, cell detection unit 10 can be of simpler configuration than that in the third embodiment.

Fifth Embodiment

Figure 14B:
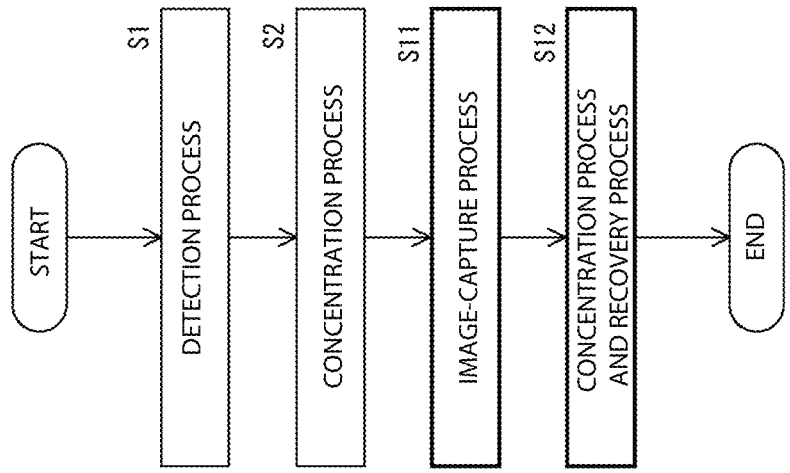
FIG. 14B is a flowchart illustrating the processes performed by the cell detection device according to the fifth embodiment.
Figure 14A:
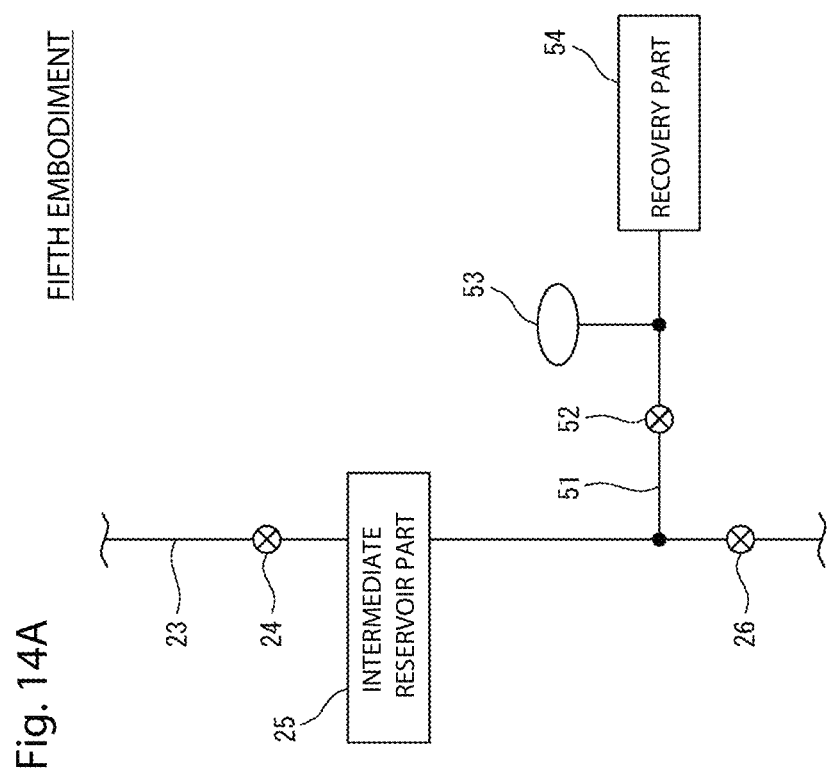
FIG. 14A is a block diagram illustrating the configuration of a cell detection device according to a fifth embodiment.

As illustrated in FIG. 14A, in the fifth embodiment, contrasted with the first embodiment, recovery flow path 51, valve 52, diaphragm pump 53, and recovery part 54 are added. The configuration of cell detection device 10 is otherwise the same as in the first embodiment.

Recovery flow path 51 connects recovery part 54 and recirculation flow path 23 between intermediate reservoir part 25 and valve 26. Valve 52 and diaphragm pump 53 are arranged in recovery flow path 51. Diaphragm pump 53 is configured such that positive pressure and negative pressure can be applied to recovery flow path 51. Driving diaphragm pump 53 using negative pressure causes the concentrated image-capture specimen accumulated in intermediate reservoir part 25 to be drawn into diaphragm pump 53. Driving diaphragm pump 53 using positive pressure causes the image-capture specimen drawn into diaphragm pump 53 to be pumped into recovery part 54.

As illustrated in FIG. 14B, in the fifth embodiment, contrasted with the first embodiment, steps S11 and S12 are added to the process in FIG. 4 in lieu of step S3.

In step S11, controller 31 performs an image-capture process. Specifically, controller 31 starts the process illustrated in FIG. 15 (described later) and the process illustrated in FIG. 5B in parallel. The image-capture specimen concentrated by intermediate reservoir part 25 is thereby resupplied to flow cell 17. Particle-image-capture part 28 then captures images of the particles contained in the image-capture specimen that has been resupplied to flow cell 17. Only particles assessed to be CTCs on the basis of the captured images are resupplied to recirculation flow path 23 and accumulated in intermediate reservoir part 25; the other particles are sent to waste fluid reservoir part 22. In step S12, controller 31 performs a concentration process and a recovery process. The image-capture specimen accumulated in intermediate reservoir part 25 is thereby concentrated. The concentrated image-capture specimen is then sent to recovery part 54 and recovered thereby. In step S12, the image-capture specimen may be recovered by recovery part 54 without having been concentrated.

Figure 15:
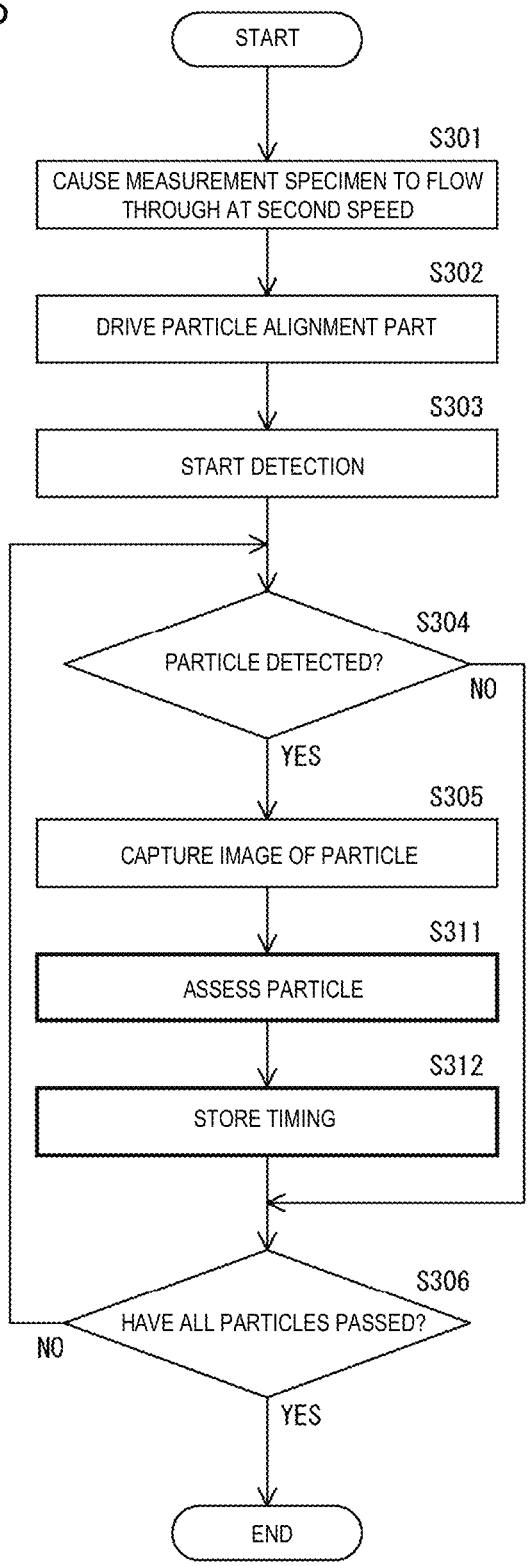
FIG. 15 is a flowchart illustrating the processes initiated by an image-capture process according to the fifth embodiment.

In the process illustrated in FIG. 15, contrasted with the process illustrated in FIG. 6A, steps S311 and S312 are added as stages subsequent to step S305.

In step S311, controller 31 analyzes the image generated in step S305, and assesses the particle illustrated in the image. Specifically, controller 31 assesses whether the particle illustrated in the image is a cell in which two luminescent points based on chromosome 17 and three or more luminescent points based on the Her2 gene are included in the nucleus; i.e., whether the particle is a CTC. In step S312, when it is assessed that the particle is a CTC, controller 31 stores the timing at which the particle passed detection position 20a.

Particles assessed to be CTCs are sent to recirculation flow path 23 by particle sorter 21 in the process illustrated in FIG. 5B. The particles assessed to be CTCs are sent to recirculation flow path 23, and the image-capture specimen containing these particles is recovered by recovery part 54 after being concentrated by intermediate reservoir part 25. Thus, when the particles assessed to be CTCs are recovered by recovery part 54, the operator can use a microscope to observe the particles assessed to be CTCs or perform other such diagnostic procedures.

Controller 31 may send the entire image-capture specimen which was re-circulated using recirculation flow path 23 and of which images were captured by particle-image-capture part 28 to recirculation flow path 23. In this case, the image-capture specimen which was re-circulated to recirculation flow path 23 and of which images were captured by particle-image-capture part 28 is concentrated by intermediate reservoir part 25 and then recovered by recovery part 54. Once this is done, the operator can confirm all of the image-captured particles with a microscope.

Sixth Embodiment

Figure 16B:
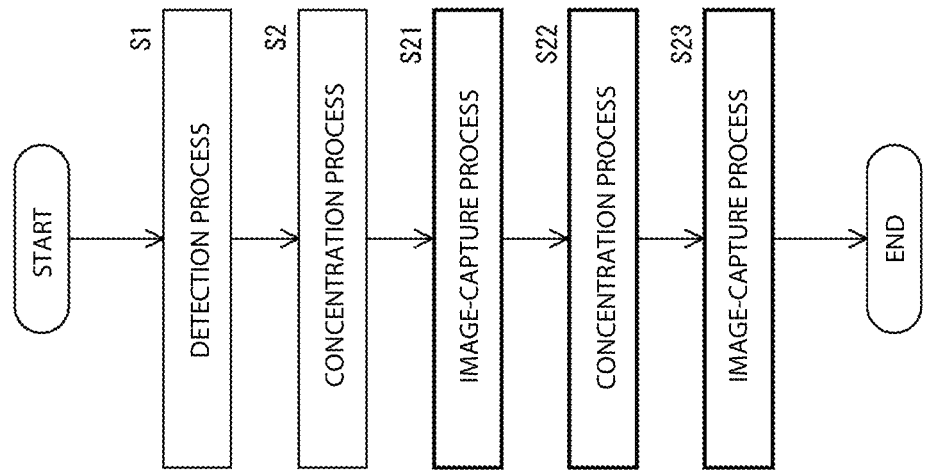
FIG. 16B is a flowchart illustrating the processes performed by a cell detection device according to the sixth embodiment.
Figure 16A:
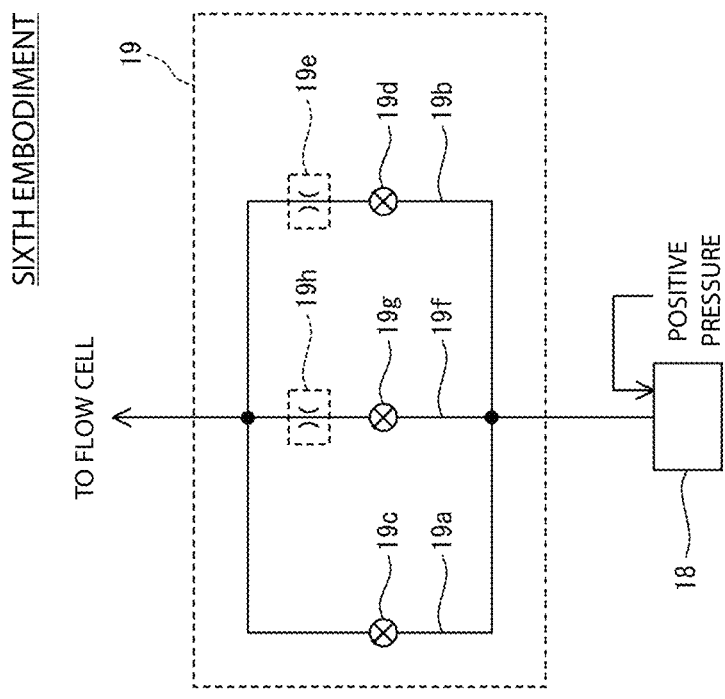
FIG. 16A is a schematic diagram illustrating the configuration of a speed-change part according to a sixth embodiment.

As illustrated in FIG. 16A, in the sixth embodiment, contrasted with the first embodiment, speed-change part 19 further comprises flow path 19f, valve 19g, and orifice 19h. The configuration of cell detection device 10 is otherwise the same as in the first embodiment.

Flow path 19f links sheath liquid supply part 18 and flow cell 17, flow path 19f being arranged in parallel with flow paths 19a, 19b. Valve 19g and orifice 19h are arranged in flow path 19f. The cross-sectional diameter of flow path 19 is equal to that of flow paths 19a, 19b. The cross-sectional diameter of orifice 19h is less than that of flow path 19f and greater than that of orifice 19e. When only valve 19g is open, the sheath liquid pumped from sheath liquid supply part 18 is supplied to flow cell 17 through flow path 19f.

Taking V3 to be the flow volume per unit time of the sheath liquid supplied to flow cell 17 when the sheath liquid passes through flow path 19f, V3 is less than V1 and greater than V2, due to orifice 19h. Therefore, taking the flow volume per unit time of the sheath liquid supplied to flow cell 17 as V1, V3, or V2, and the speeds of the measurement specimen flowing through flow path 17a to be first, second, and third speeds, respectively, the second speed is lower than the first speed and higher than the third speed.

As illustrated in FIG. 16B, in the sixth embodiment, contrasted with the first embodiment, steps S21-23 are added in lieu of step S3 in the process of FIG. 4.

In step S21, controller 31 performs an image-capture process. Specifically, controller 31 starts the process illustrated in FIG. 15 and the process illustrated in FIG. 5B in parallel. The image-capture specimen concentrated by intermediate reservoir part 25 is thereby resupplied to flow cell 17. Particle-image-capture part 28 captures images of the particles contained in the image-capture specimen that has been resupplied to flow cell 17. Only particles assessed to be CTCs on the basis of the captured images are sent to recirculation flow path 23; the other particles are sent to waste fluid reservoir part 22.

In step S22, controller 31 concentrates the image-capture specimen that contains only particles assessed to be CTCs using intermediate reservoir part 25. In step S23, controller 31 performs an image-capture process. Specifically, controller 31 starts the process illustrated in FIG. 17. The image-capture specimen concentrated by intermediate reservoir part 25 is thereby resupplied to flow cell 17. Particle-image-capture part 28 then captures images of the particles contained in the image-capture specimen that has been resupplied to flow cell 17. The image-capture specimen of which images were captured in step S23 is sent to waste fluid reservoir part 22. The image-capture specimen of which images are captured in step S23 may be recovered by a recovery part such as is illustrated in FIG. 14A.

Figure 17:
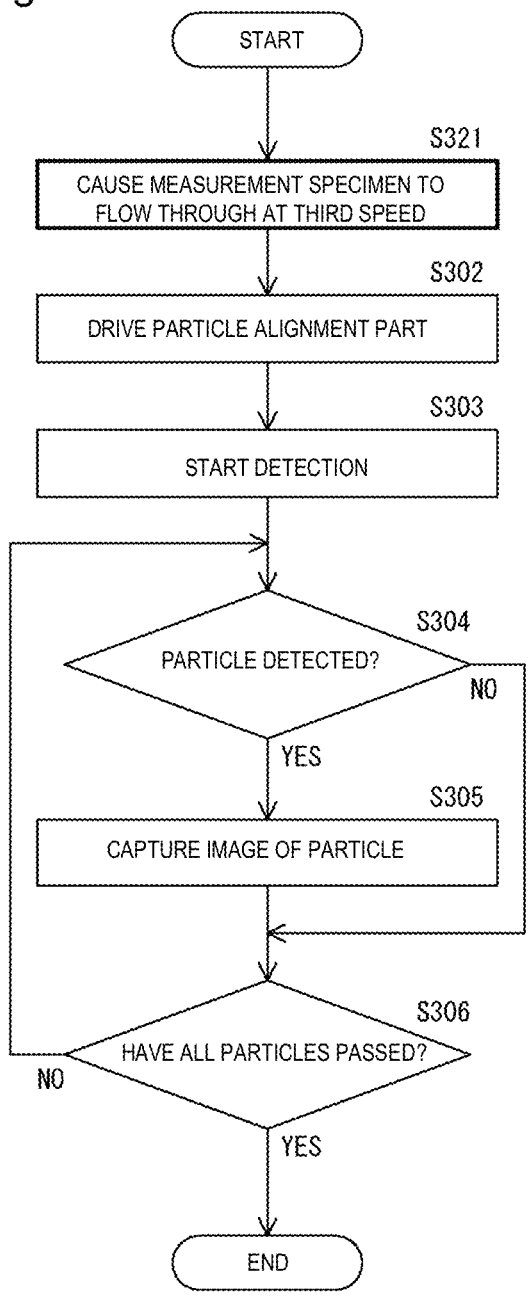
FIG. 17 is a flowchart illustrating the processes initiated by an image-capture process according to the sixth embodiment.

In the process illustrated in FIG. 17, contrasted with the process illustrated in FIG. 6A, step 321 is added in lieu of step S301. In step S321, controller 31 causes the image-capture specimen concentrated by intermediate reservoir part 25 to flow into flow cell 17 at the third speed, which is lower than the second speed.

Thus, since the particles assessed to be CTCs in the second round are furthermore caused to flow into flow cell 17 at low speed in the third round, it is possible to capture high-resolution images of only particles assessed to be CTCs. Additionally, prior to the image-capture in the third round, a CTC assessment is performed at high speed in the second round, and particles that are not CTCs are excluded. This makes it possible to keep the processing time for the entire process short, even when image-capture is performed at low speed in the third round.

The operator may be allowed to set whether image-capture is performed at the third speed. When image-capture is not performed at the third speed, it is instead performed at the second speed. Alternatively, controller 31 may be configured so as to determine whether image-capture is performed at the third speed on the basis of the result of analysis of image-capture at the second speed. In this configuration, when it is determined that image-capture is not to be performed at the third speed, controller 31 executes a process in which the image-capture specimen concentrated in step S22 of FIG. 16B is recovered using recovery part 54, in the same manner as in, e.g., the fifth embodiment. There may be four or more speeds at which the measurement specimen and the image-capture specimen are caused to flow through flow cell 17.

Seventh Embodiment

The test cells are not limited to being CTCs. When assessing illness and confirming medication, it is also effective to detect and capture images of circulating endothelial cells (CECs), endothelial progenitor cells (EPCs), mesenchymal stem cells (MSCs), hematopoietic stem cells (HSCs), antigen-specific T-cells, and the like. Such cells can be detected by specifically bonding fluorescence-labeled antibodies to surface antigens expressed in these cells. The test cells are detected by analyzing captured images that are captured by particle-image-capture part 28, in the same manner as in the first embodiment.

In the seventh embodiment, by further confirming the cell-interior state of signal molecules included in the test cells, the state of activation of the test cells is assessed. It is possible to evaluate the functionality of the test cells through the behavior of the signal molecules. Signal molecules are detected by specifically bonding fluorescence-labeled antibodies thereto. By confirming the state of the detected signal molecules, the state of activation of the test cells and other attributes are assessed. Detection of the signal molecules and assessment, inter alia, of the activation state thereof are performed by analyzing captured images that are captured by particle-image-capture part 28.

The dye used in fluorescence-labeling of the test cells and the signal molecules may be one of the dyes described in the first embodiment, or may be another dye. The reagents used in the preparation of the measurement sample are changed in accordance with the antibodies and the dyes used in the fluorescence-labeling. The wavelength of the light that excites the dye may comprise a single wavelength as described in the first embodiment, or may comprise different wavelengths. When the wavelengths at which fluorescence is excited from the dyes differ from each other, light source 121 comprises a stroboscopic laser, as illustrated in, e.g., FIG. 2.

In the seventh embodiment, sorting of test cells through the flowcharts in FIG. 5A and FIG. 5B is performed first, the same as in the first embodiment.

In cases where the test cells are CECs, EPCs, or MSCs, prescribed reagents are admixed into a sample when preparing a measurement specimen. The reagents to be admixed include: reagents that cause hemolysis of red blood cells; reagents containing CD45 labeled antibodies for detecting white blood cells; reagents containing antibodies that specifically bond to surface antigens expressed in the test cells, the antibodies being fluorescence-labeled using dyes; reagents containing antibodies that specifically bond to signal molecules, the antibodies being fluorescence-labeled using dyes; and reagents that stain nuclei. Similarly to the first embodiment, the reagents that cause hemolysis of red blood cells may be omitted.

In step S103 of FIG. 5A, controller 31 executes the same process as in the first embodiment. When the intensity of fluorescence is equal to or less than a prescribed threshold value, and the intensity of forward scattered light is equal to or greater than a prescribed threshold value, controller 31 assesses there to be a strong possibility that the particle at detection position 20*a* is a test cell; i.e., a CEC, EPC, or MSC. Because particles that are test cells do not bond to the CD45 labeled antibodies, the intensity of the fluorescence is equal to or less than the prescribed threshold value. In step S103, in cases where the detected particles are particles other than white blood cells, and in cases where the detected particles are large, controller 31 assesses there to be a strong possibility that the detected particles are test cells; i.e., CECs, EPCs, or MSCs.

In cases where the test cells are HSCs, prescribed reagents are admixed into a sample when preparing a measurement specimen. The reagents to be admixed include: reagents that cause hemolysis of red blood cells; reagents containing labeled antibodies for detecting all of the blood cells that differentiate from the HSC; reagents containing antibodies that specifically bond to surface antigens expressed in the HSC, the antibodies being fluorescence-labeled using dyes; reagents containing antibodies that specifically bond to signal molecules in the HSC, the antibodies being fluorescence-labeled using dyes; and reagents that stain nuclei. The reagents containing labeled antibodies for detecting all of the blood cells that differentiate from the HSCs are typically referred to as "lineage markers." Each of the lineage marker antibodies are labeled using the same dye. Similarly to the first embodiment, the reagents that cause hemolysis of red blood cells may be omitted.

In step S103 of FIG. 5A, when the intensity of fluorescence is equal to or less than a prescribed threshold value, and the intensity of forward scattered light is equal to or greater than a prescribed threshold value, controller 31 assesses there to be a strong possibility that the particle at detection position 20*a* is a test cell; i.e., a HSC. Because particles that are test cells do not bond to the lineage markers, the intensity of the fluorescence is equal to or less than the prescribed threshold value. Additionally, HSCs are larger than any of the other blood cells that differentiate from the HSCs. Therefore, in step S103, in cases where the intensity of the fluorescence is equal to or less than the prescribed threshold value, and in cases where the intensity of the forward scattered light is equal to or greater than the prescribed threshold value, there is a strong possibility that the particle at detection position 20*a* is a HSC.

In cases where the test cells are antigen-specific T-cells, prescribed reagents are admixed into a sample when preparing a measurement specimen. The reagents to be admixed include: agents that cause hemolysis of red blood cells; reagents in which CD2 and CD3 antibodies are removed from the lineage markers; reagents containing CD3 labeled antibodies that specifically bond to surface antigens expressed in T-cells; reagents containing MHC tetramers that specifically bond to surface antigens expressed in antigen-specific T-cells from among the T-cells, the MHC tetramers being labeled using dyes; reagents containing antibodies that specifically bond to signal molecules in the antigen-specific T-cells, the antibodies being fluorescence-labeled using dyes; and reagents that stain nuclei. The antibodies in which CD2 and CD3 antibodies are removed from the lineage markers are labeled using the same dye. Similarly to the first embodiment, the reagents that cause hemolysis of red blood cells may be omitted.

In step S103 of FIG. 5A, when the intensity of fluorescence is equal to or less than a prescribed threshold value, controller 31 assesses there to be a strong possibility that the particle at detection position 20*a* is a T-cell. Because particles that are T-cells do not bond to the lineage markers, the intensity of the fluorescence is equal to or less than the prescribed threshold value. Therefore, in step S104, in cases where the intensity of the fluorescence is equal to or less than the prescribed threshold value, there is a strong possibility that the particle at detection position 20*a* is a T-cell.

Controller 31 then executes the process in FIG. 5B on those particles for which the assessment as to whether there is a strong possibility that the particles are test cells has been performed. The particles that are assessed to be highly likely to be test cells are thereby sent to recirculation flow path 23 through flow path 17*c*. Upon concentration being performed by intermediate reservoir part 25, controller 31 resupplies the image-capture specimen to flow cell 17, and, in executing the process illustrated in FIG. 6A, sequentially captures images of the particles that are highly likely to be test cells.

Using the processes described above, controller 31 generates images of the particles that are highly likely to be test cells; i.e., CECs, EPCs, MSCs, HSCs, or antigen-specific T-cells. The generated images include images of the fluorescence of the labeled antibodies that specifically bond to the surface antigens expressed in the test cells, and images of the fluorescence of the labeled antibodies that specifically bond to the signal molecules in the test cells. Cameras 129-131 receive the fluorescence of different wavelengths produced by the labeled antibodies, and output image information for each of the wavelengths of fluorescence. In the case of the configuration in FIG. 8, bright-field images of the particles are also generated on the basis of image-capture signals from camera 142.

When the image-capture process ends, the operator inputs a results-display command to cell detection device 10 via input unit 33.

As illustrated in FIG. 18, when a results-display command has been inputted by the operator and an assessment of "YES" is obtained in step S411, then in step S412 controller 31 analyzes all of the captured particle images, and extracts test cells.

In cases where the test cells are CECs, EPCs, MSCs, or HSCs, in step S412, controller 31 refers, for each of the particles, to images including the label dye that specifically bonds to antibodies expressed in the test cells, and assesses whether the images include regions in which the fluorescence exceeds a prescribed intensity. In cases where the images include regions of fluorescence, controller 31 assesses that the particles to be assessed are test cells.

In cases where the test cells are antigen-specific T-cells, in step S412, controller 31 first refers, for each of the particles, to images including the CD3 label dye that specifically bonds to antibodies expressed in the T-cells, and assesses whether the images include regions in which the fluorescence exceeds a prescribed intensity. In cases where the images include regions of fluorescence, controller 31 assesses that the particles to be assessed are T-cells. Furthermore, controller 31 refers, for each of the particles assessed to be T-cells, to images including the dye that labels MHC tetramers that bond to surface antigens expressed in the antigen-specific T-cells, and assesses whether the images include regions in which the fluorescence exceeds a prescribed intensity. In cases where the images include regions of fluorescence, controller 31 assesses that the particles to be assessed are antigen-specific T-cells.

Furthermore, in step S413, controller 31 analyzes the images of the extracted test cells, assesses whether each of the cells has been activated, and extracts activated test cells. Controller 31 refers to images including the label dye that specifically bonds to the signal molecules, and detects the state of the signal molecules in the cells. Controller 31 assesses whether the test cells have been activated on the basis of the detected state of the signal molecules.

For example, in cases where the test cells are CECs, the signal molecules can be designated as NFκB. In step S413, controller 31 assesses whether the CECs have been activated according to whether the NFκB serving as the signal molecules is localized in the nucleus. CECs detach from the walls of blood vessels and flow into the blood. CEC detachment may be due to stimulation caused by inflammation, but also to changes in pressure caused by compression or the like. Controller 31 assesses that stimulation caused by inflammation is the cause for detachment according to whether the NFκB serving as the signal molecules is localized in the nucleus. Controller 31 extracts CECs that have detached due to stimulation caused by inflammation as activated CECs.

Figure 19A:
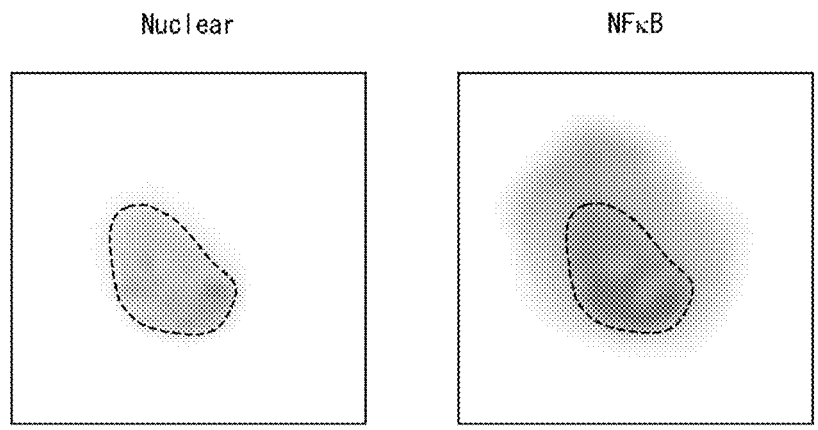
FIG. 19A is a diagram illustrating a screen of a CEC assessed to have been activated according to the seventh embodiment.

As illustrated in FIG. 19A, in CECs that have detached due to stimulation caused by inflammation, the NFκB tends to be localized in the nucleus. The left-side image in FIG. 19A illustrates a fluorescence image of the nucleus. For expediency, the left-side image in FIG. 19A additionally includes dotted lines that illustrate the outline of the nucleus. The right-side image in FIG. 19A illustrates a fluorescence image of the NFκB serving as the signal molecules, and furthermore includes a dotted-line region that corresponds to the nucleus in the left-side image. In each of the left-side image and the right-side image in FIG. 19A, the intensity of the fluorescence from the nucleus and the fluorescence from the NFκB increase correspondingly with respect to increased darkness of the images. In the example in FIG. 19A, it is apparent that the NFκB serving as the signal molecules is localized in the nucleus.

Figure 19B:
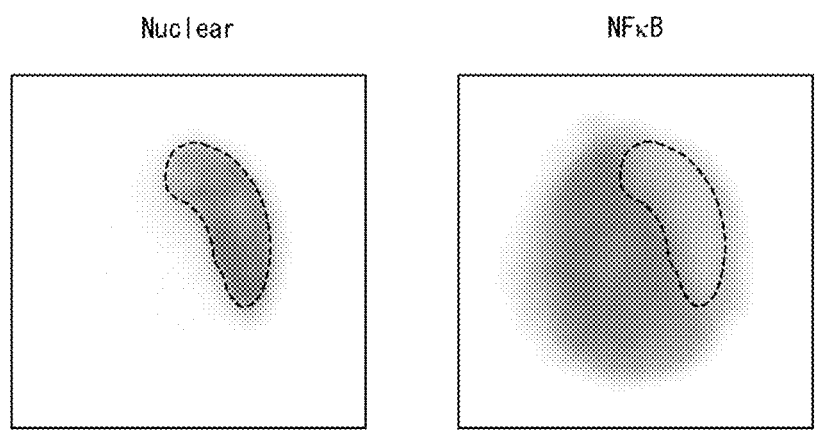
FIG. 19B is a diagram illustrating a screen of a CEC assessed to have not been activated according to the seventh embodiment.

In the example in FIG. 19B, the NFκB serving as the signal molecules is not localized in the nucleus. In the right-side image in FIG. 19B, the dotted-line region is a region of the nucleus. Thus, in CECs that have detached due to stimulation other than that caused by inflammation, the NFκB tends not to be localized in the nucleus. Controller 31 analyzes the fluorescence images of the signal molecules, and assesses whether the CEC have been activated according to whether the NFκB serving as the signal molecules is localized in the nucleus.

In cases where the test cells are EPCs, MSCs, HSCs, or antigen-specific T-cells, controller 31 similarly evaluates the functionality of these cells on the basis of the localization position of the signal molecules, and extracts cells that have been amplified as a result of damage or the like as activated cells. For example, in cases where the test cells are EPCs or MSCs, controller 31 evaluates the reparability of the cells on the basis of the localization position of the signal molecules, and extracts cells having high reparability as activated cells.

The evaluation of the functionality of the test cells is not limited to the localization position of the signal molecules; other factors may be used in the evaluation as well. The type of signal molecule can be changed as appropriate in accordance with the factor used in the evaluation of functionality.

Returning to FIG. 18, in step S414, controller 31 displays the number of test cells extracted in steps S412 and S413, and the number of activated test cells, on output unit 34. In step S415, controller 31 displays images of the test cells on output unit 34. For example, in cases where the test cells are CECs, in steps S414 and S415, output unit 34 displays screens 60 illustrated in FIG. 20A and FIG. 20B.

Screens 60 display the number of CECs, the number of activated CECs, and the images of the CECs. The operator can know whether the amount of CECs in the blood has increased by referring to the number of CECs. Additionally, the operator can ascertain the proportion of active-state CECs by referring to the number of activated CECs. This information can be useful for a physician, etc., to determine guidelines for therapy.

The two images arranged in the horizontal direction are images of the same particle. Image 61 illustrates the fluorescence produced by the labeled antibodies that specifically bond to the nucleus, and image 62 illustrates the fluorescence produced by the labeled antibodies that specifically bond to the signal molecules. As described above, the signal molecules are NFκB, which is a protein contained in CEC. CD146 labeled antibodies that specifically bond to the antigens expressed in the CECs are used in the detection of CECs. Images 61, 62 are inverted in tone, and then converted to grayscale. Bright-field images may also be included on screen 60 together with images 61, 62.

Figure 20A:
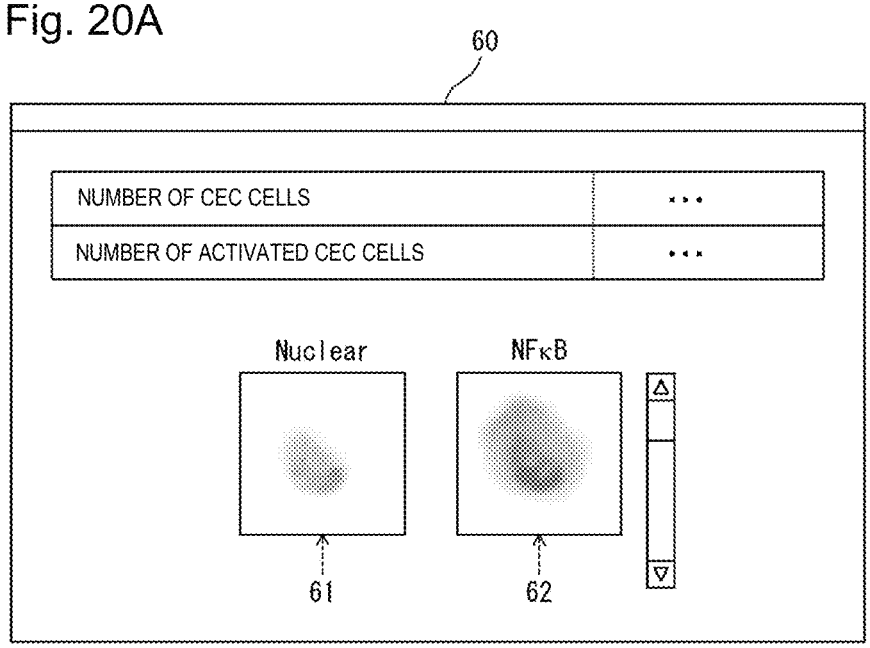
FIG. 20A and FIG. 20B are diagrams illustrating screens displayed by an output unit according to the seventh embodiment.
Figure 20B:
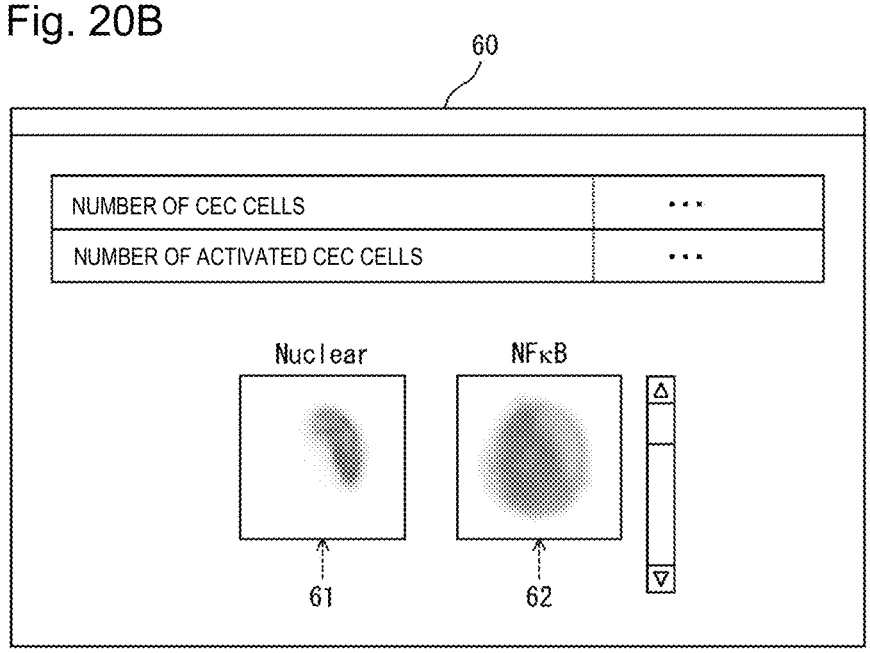

The particle images illustrated in FIG. 20A illustrate CECs that have been activated, and the particle images illustrated in FIG. 20B illustrate CECs that have not been activated. In cases where there are multiple images of CEC particles, the operator can switch between and display particle images on screen 60. Furthermore, screen 60 may alternatively be provided with a button, etc., with which it is possible to individually display images of CECs that have been activated and images of CEC that have not been activated.

In the seventh embodiment, images are obtained of cells that are useful in the assessment of illness and the confirmation of medication, the cells being CECs, EPCs, MSCs, HSCs, antigen-specific T-cells, or the like rather than CTCs. These cell images are displayed, together with the number of extracted cells, as needed by an operator. The displayed information can be of use for a physician, etc., to determine guidelines for therapy.

For example, in patients afflicted with myocardial infarction or cerebral infarction, the number of CECs is increased to a greater extent than in healthy subjects. Additionally, when there is tissue damage, the number of EPCs and MSCs is increased to a greater extent than in healthy subjects. Therefore, ascertaining the number of such cells makes it possible for a physician, etc., to ascertain the possibility that a patient is afflicted with myocardial infarction or another such condition, or the possibility that the patient has suffered tissue damage.

Furthermore, in the seventh embodiment, the activation state of the CECs, EPCs, MSCs, HSCs, or antigen-specific T-cells is detected and displayed on the basis of the behavior of signal molecules. Thus, by also displaying the activation state of the test cells, the specificity of the detection results of the test cells can be further enhanced.

For example, in cases where the test cells are CECs, the number of activated CECs is displayed together with the number of CECs, as illustrated in FIG. 20A and FIG. 20B. This makes it possible for a physician, etc., to correctly ascertain the number of CECs that have detached due to stimulation caused by inflammation, and to more precisely ascertain the possibility that a patient is afflicted with myocardial infarction or another such condition. Additionally, of late, T-cells corresponding to specific antigens have been utilized in immunotherapy. For example, trials are currently being performed on therapeutic methods involving T-cells that can specifically respond to cancerous cells being returned into the blood, and the potency of these T-cells being monitored. In the seventh embodiment, it is possible for the activation state of antigen-specific T-cells to be presented using cell images and the number of cells to a physician, etc., during such monitoring. This makes it possible for a physician, etc., to confirm the immunotherapeutic effect of the T-cells.

Eighth Embodiment

In the eighth embodiment, particles assessed to be CTCs and particles assessed to be CECs are recovered. In the eighth embodiment, contrasted with the first embodiment, reagents for detecting the CECs described in the seventh embodiment are additionally admixed when preparing a measurement specimen. Additionally, in the eighth embodiment, light source 121 is configured so as to emit light of two types of wavelength, for capturing images of CTCs and CECs, respectively.

Figure 21:
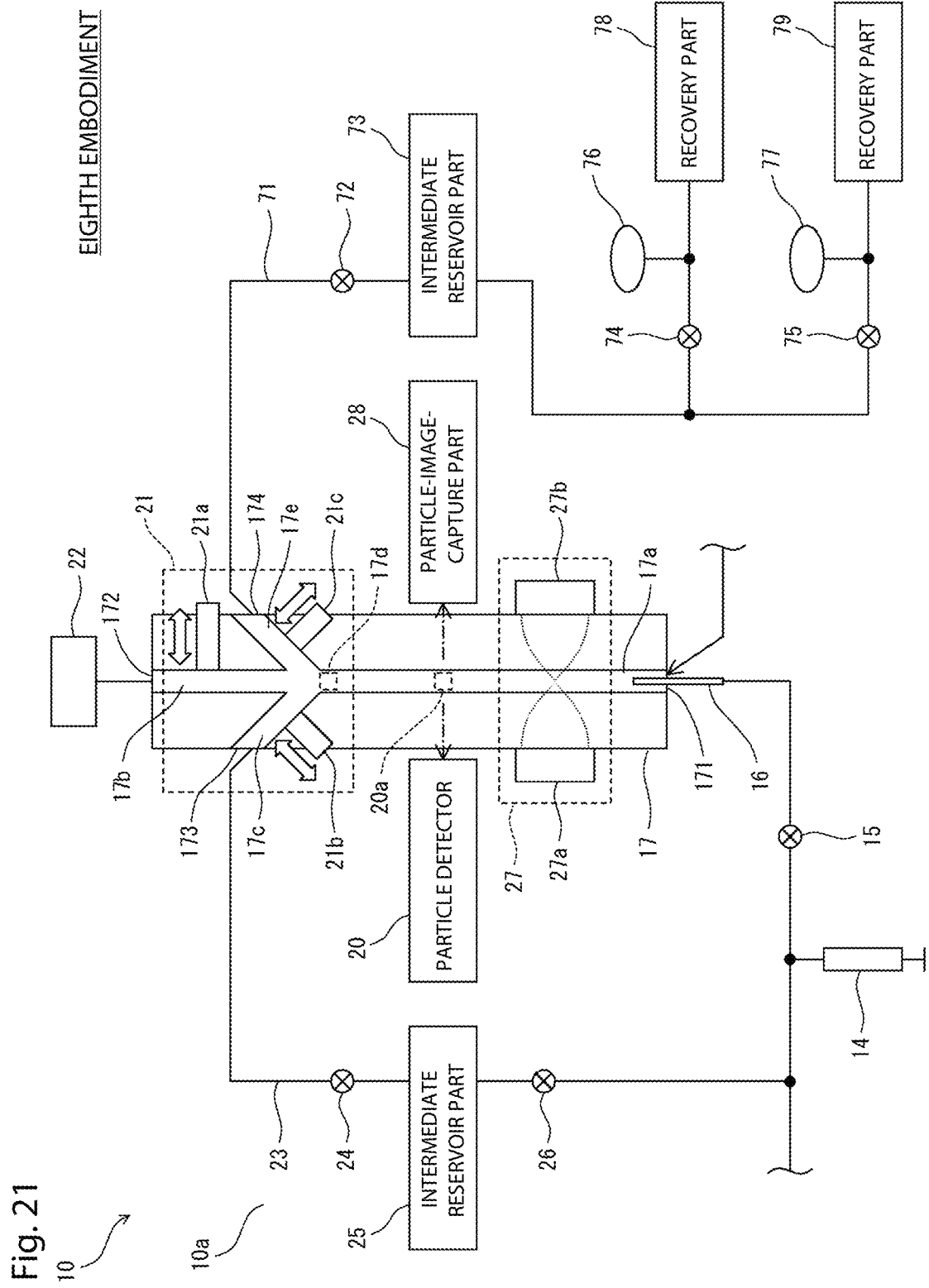
FIG. 21 is a schematic diagram illustrating the configuration of a cell detection device according to an eighth embodiment.

As illustrated in FIG. 21, in the eighth embodiment, contrasted with the first embodiment, flow cell 17 further comprises recovery outlet 174, and flow path 17e in the interior. Flow path 17e branches from flow path 17a at a position between flow path 17a and flow path 17b, and is linked to recovery outlet 174. Particle sorter 21 furthermore comprises members 21b, 21c. Cell detection device 10 further comprises recovery flow path 71, valve 72, intermediate reservoir part 73, valves 74, 75, diaphragm pumps 76, 77, and recovery parts 78, 79. Recovery flow path 71 is linked to recovery outlet 174 of flow cell 17. The configuration of cell detection device 10 is otherwise the same as in the first embodiment.

Particle sorter 21 causes members 21b, 21c to project toward flow paths 17c, 17e, respectively. When member 21a is positioned at such a position that flow path 17b is opened, particles at branch position 17d are sent to waste fluid reservoir part 22 via flow path 17b. When member 21b is positioned at such a position that flow path 17c is opened, and when members 21a, 21c are positioned at such positions that flow paths 17b, 17e, respectively, are closed, particles at branch position 17d are sent to recirculation flow path 23 via flow path 17c. When member 21c is positioned at such a position that flow path 17e is opened, and when members 21a, 21b are positioned at such positions that flow paths 17b, 17c, respectively, are closed, particles at branch position 17d are sent to recovery flow path 71 via flow path 17e.

Figure 22:
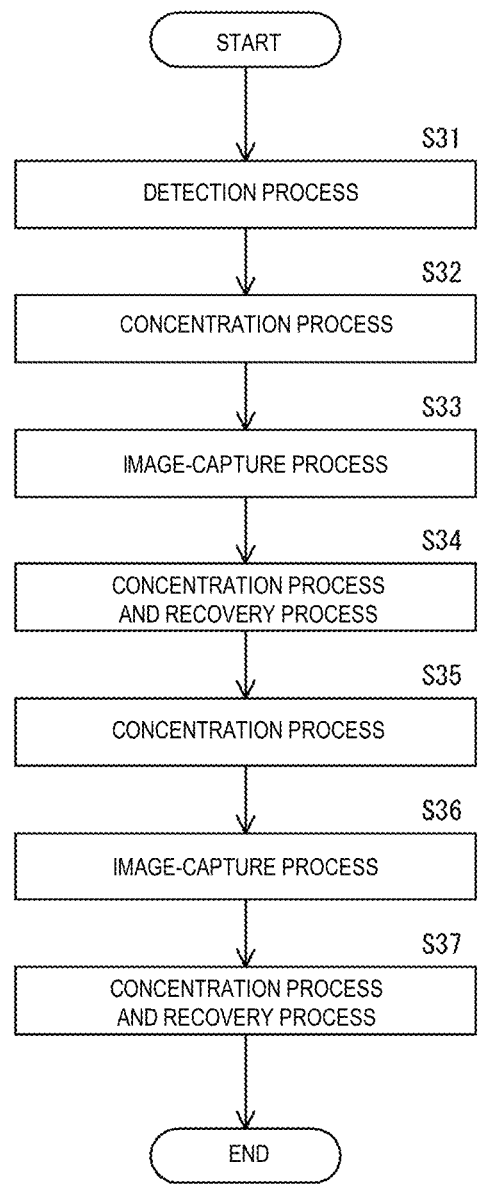
FIG. 22 is a flowchart illustrating the processes performed by the cell detection device according to the eighth embodiment.

As illustrated in FIG. 22, when a start command is inputted by an operator, controller 31 performs a detection process in step S31. The measurement specimen in specimen container 10b is thereby supplied to flow cell 17, and the particles contained in the measurement specimen are detected by particle detector 20. On the basis of fluorescence and forward scattered light received by light-reception part 108, an assessment is made as to whether there is a strong possibility that the particle positioned at detection position 20a is a CTC or a CEC. Specifically, when the intensity of fluorescence at wavelength λ2 is equal to or less than a prescribed threshold value, and the intensity of forward scattered light at wavelength λ1 is equal to or greater than a prescribed threshold value, controller 31 assesses that the particle at detection position 20a is highly likely to be a CTC or a CEC.

The particles that are highly likely to be CTCs or CECs are sent to recirculation flow path 23 through flow path 17c. The other particles are sent to waste fluid reservoir part 22 through flow path 17b. In step S32, controller 31 concentrates the image-capture specimen sent to recirculation flow path 23 using intermediate reservoir part 25.

In step S33, controller 31 performs an image-capture process. The image-capture specimen concentrated by intermediate reservoir part 25 is thereby resupplied to flow cell 17, and particle-image-capture part 28 captures images of the particles contained in the image-capture specimen. At this time, light source 121 emits light at a wavelength for capturing images of CTCs. An assessment is made as to whether the particles are CTCs on the basis of the fluorescence images acquired using particle-image-capture part 28. Particles assessed to be CTCs are sent to recovery flow path 71 through flow path 17e. Particles assessed to not be CTCs are sent to recirculation flow path 23 through flow path 17c.

In step S34, controller 31 performs a process in which the image-capture specimen sent to recovery flow path 71 is concentrated using intermediate reservoir part 73, and the image-capture specimen concentrated by intermediate reservoir part 73 is recovered using recovery part 78. The particles assessed to be CTCs are thereby recovered by recovery part 78. However, in step S35, controller 31 concentrates the image-capture specimen sent to recirculation flow path 23 using intermediate reservoir part 25.

In step S36, controller 31 performs an image-capture process. The image-capture specimen concentrated by intermediate reservoir part 25 is thereby resupplied to flow cell 17, and particle-image-capture part 28 captures images of the particles contained in the image-capture specimen. At this time, light source 121 emits light at a wavelength for capturing images of CECs. An assessment is made as to whether the particles are CEC on the basis of the fluorescence images acquired using particle-image-capture part 28. Particles assessed to be CECs are sent to recovery flow path 71 through flow path 17e. Particles assessed to not be CEC are sent to waste fluid reservoir part 22 through flow path 17b.

In step S37, controller 31 performs a process in which the image-capture specimen sent to recovery flow path 71 is concentrated using intermediate reservoir part 73, and the image-capture specimen concentrated by intermediate reservoir part 73 is recovered using recovery part 79. The particles assessed to be CECs are thereby recovered by recovery part 79.

According to the eighth embodiment, the first operation performed by cell detection device 10 makes it possible to acquire images of CTCs and images of CECs, and furthermore to individually recover CTCs and CECs. This makes it possible to cause operator labor to be reduced, and the amount of time required for processing to be shortened, to a greater extent than in cases where image-capture and recovery of CTCs and image-capture and recovery of CECs are performed separately. The recovered particles are not limited to CTCs and CECs; such particles may be EPCs, etc., or even other types of particles.

According to the configuration described in the Patent Document 1, when the speed of the particles flowing through the flow cell is reduced in order to increase the quality of the particle images, a large quantity of the measurement specimen must be measured in cases where an image is to be acquired of cells that are included in a measurement specimen in negligible amounts; e.g., one per several 100,000 cells. A drawback is accordingly presented in that a very long time is required to acquire the cell image.

According to the embodiments above, it is possible to efficiently acquire images of cells to be measured.

The invention claimed is:
1. A sample analysis method, comprising:
introducing a measurement specimen to a flow cell through an inlet;
sensing cells in the measurement specimen at a first position in the flow cell;

directing target cells among the cells sensed at the first position, to a recirculation flow path at a second position that is downstream of the first position, wherein the recirculation flow path connects the second position and the inlet;

supplying the target cells to the flow cell via the recirculation flow path; and capturing images of the target cells in the flow cell, wherein the recirculation flow path comprises an intermediate reservoir adapted to increase a concentration of the target cells.

2. The method according to claim 1, wherein the intermediate reservoir comprises an elutriator rotor, a centrifuge or a filter.

3. The method according to claim 1, wherein the sensing comprises reading an optical characteristics of individual cells.

4. The method according to claim 3, wherein the reading comprises:
irradiating light onto the cells in the measurement specimen passing the first position; and
detecting a scattered light and a fluorescence emitted from the individual cells.

5. The method according to claim 1, wherein
a width of a flow path in the flow cell in a first direction perpendicular to a direction in which the measurement specimen flows is greater than a width of the flow path in a second direction perpendicular to the first direction; and
the target cells are imaged, facing to the second direction.

6. The method according to claim 1, wherein
an imaging device is coupled to the flow cell and controlled to capture images of individual cells at the first position for sensing cells, and
the imaging device is controlled to capture images of the target cells supplied from the recirculation flow path.

7. The method according to claim 1, wherein
the measurement specimen is introduced to the flow cell with a first flow speed, and
the target cells are supplied from the recirculation flow path to the flow cell with a second flow speed that is reduced than the first flow speed.

8. The method according to claim 1, wherein
the flow cell is connected to a reservoir storing a sheath liquid, and
a flow speed of the target cells in the flow cell is reduced by increasing a volume of the sheath liquid supplied to the flow cell.

9. The method according to claim 1, further comprising applying an ultra sound to the flow cell so that the target cells flowing in the flow cell are aligned.

10. The method according to claim 1, further comprising collecting the target cells at a downstream of the flow cell.

11. The method according to claim 1, wherein the target cells comprise circulating tumor cell (CTC), Circulating Endothelial Cell (CEC), Endothelial Progenitor Cell (EPC), Mesenchymal Stem Cell (MSC), Hematopoietic Stem Cell (HSC) or antibody-specific T cell.

12. The method according to claim 1, further comprising mixing a biological sample collected from a patient and a reagent to prepare a measurement specimen.

13. The method according to claim 12, wherein the reagent contains a labeled antibody which binds to a specific site of the target cell.

14. The method according to claim 12, wherein the reagent contains a nucleic acid probe which hybridizes to a specific site of a nucleic acid in the target cell.

15. The method according to claim 12, wherein the biological sample comprises a peripheral blood and the reagent contains a hemolytic agent to hemolyze red blood cells.

16. A sample analysis method, comprising:
introducing a measurement specimen to a flow cell through an inlet;
irradiating light onto the flow cell and reading an optical response from individual particles in the measurement specimen flowing inside the flow cell;
actuating a particle sorter that is coupled to a downstream of the flow cell, in response to an optical response indicative of a target cell, to change a direction of the target cell;
re-introducing the target cell, through a recirculation flow path connecting a downstream of the particle sorter and the inlet, to the flow cell; and
capturing, by an imaging device, an image of the target cell in the flow cell.

17. The method according to claim 16, wherein
the target cell presents as plural target cells in the measurement specimen, and
the plural target cells are accumulated in the recirculation flow path and then introduced to the flow cell.

18. A sample analyzer, comprising:
a flow cell to receive a measurement specimen flowing through an inlet;
a particle detector operable to sense cells in the measurement specimen at a first position in the flow cell;
a particle sorter, positioned at a second position downstream to the first position, operable to change a direction of target cells among the cells sensed at the first position;
a recirculation flow path connecting the inlet and a downstream of the particle sorter to receive the target cells directed by the particle sorter and to supply the target cells to the flow cell; and
an imaging device coupled to the flow cell to capture images of the target cells, wherein
the recirculation flow path comprises an intermediate reservoir adapted to increase a concentration of the target cells.

19. A sample analysis method, comprising:
introducing a measurement specimen to a flow cell through an inlet;
sensing cells in the measurement specimen at a first position in the flow cell;
directing target cells among the cells sensed at the first position, to a recirculation flow path at a second position that is downstream of the first position, wherein the recirculation flow path connects the second position and the inlet;
supplying the target cells to the flow cell via the recirculation flow path; and capturing images of the target cells in the flow cell, wherein
an imaging device is coupled to the flow cell and controlled to capture images of individual cells at the first position for sensing cells, and
the imaging device is controlled to capture images of the target cells supplied from the recirculation flow path.

20. A sample analysis method, comprising:
introducing a measurement specimen to a flow cell through an inlet;

sensing cells in the measurement specimen at a first position in the flow cell;

directing target cells among the cells sensed at the first position, to a recirculation flow path at a second position that is downstream of the first position, wherein the recirculation flow path connects the second position and the inlet;

supplying the target cells to the flow cell via the recirculation flow path; and capturing images of the target cells in the flow cell, wherein the measurement specimen is introduced to the flow cell with a first flow speed, and the target cells are supplied from the recirculation flow path to the flow cell with a second flow speed that is reduced than the first flow speed.

* * * * *